(12) United States Patent  
Schoenbach et al.

(10) Patent No.: US 8,000,813 B2
(45) Date of Patent: Aug. 16, 2011

(54) ULTRAWIDEBAND ANTENNA FOR OPERATION IN TISSUE

(75) Inventors: Karl H. Schoenbach, Norfolk, VA (US); Stephen Beebe, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 552 days.

(21) Appl. No.: 12/089,973

(22) PCT Filed: Aug. 21, 2006

(86) PCT No.: PCT/US2006/032440
§ 371 (c)(1),
(2), (4) Date: Aug. 5, 2008

(87) PCT Pub. No.: WO2007/024734
PCT Pub. Date: Mar. 1, 2007

(65) Prior Publication Data
US 2009/0125091 A1    May 14, 2009

Related U.S. Application Data

(60) Provisional application No. 60/709,527, filed on Aug. 19, 2005, provisional application No. 60/800,729, filed on May 16, 2006.

(51) Int. Cl.
*A61N 1/00* (2006.01)

(52) U.S. Cl. .......................................... 607/154
(58) Field of Classification Search ............... 607/2, 154
See application file for complete search history.

(56) References Cited

U.S. PATENT DOCUMENTS

| 3,591,882 | A | 7/1971 | Pearsall |
| 4,640,280 | A | 2/1987 | Sterzer |
| 4,764,473 | A | 8/1988 | Matschke et al. |
| 5,087,438 | A | 2/1992 | Gorgon |
| 6,425,851 | B1 | 7/2002 | Kiontke |
| 7,016,725 | B2 * | 3/2006 | Palti .................. 607/2 |

FOREIGN PATENT DOCUMENTS

WO    WO 89/07468    8/1989

OTHER PUBLICATIONS

Guy, et al., "Therapeutic Applications of Electromagnetic Power," IEEE, vol. 62, No. 1, Jan. 1974.
Extended European Search Report, EPO, Jul. 7, 2009.

* cited by examiner

*Primary Examiner* — George Manuel
(74) *Attorney, Agent, or Firm* — Novak Druce + Quigg LLP

(57) ABSTRACT

Method and apparatus for cellular and intracellular manipulation of cell functions with ultrashort electrical pulses and for targeted delivery of the electrical pulses into cell cultures, patients, and tissues.

44 Claims, 24 Drawing Sheets

ANTENNA DESIGN & PROTOTYPE

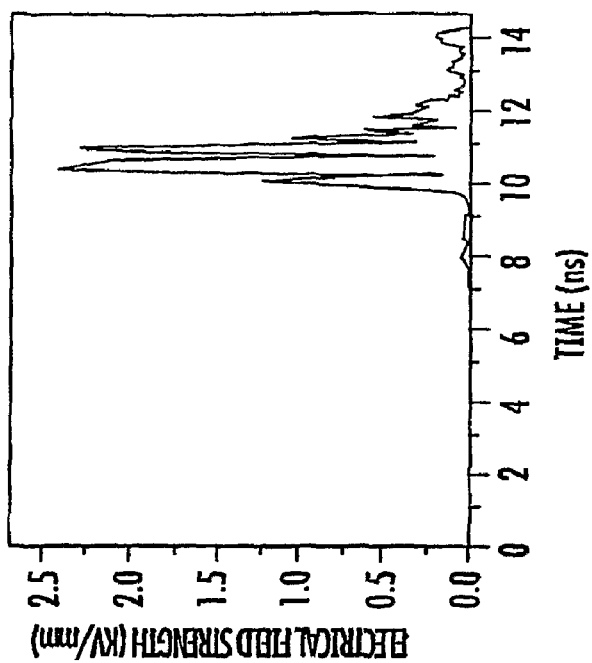
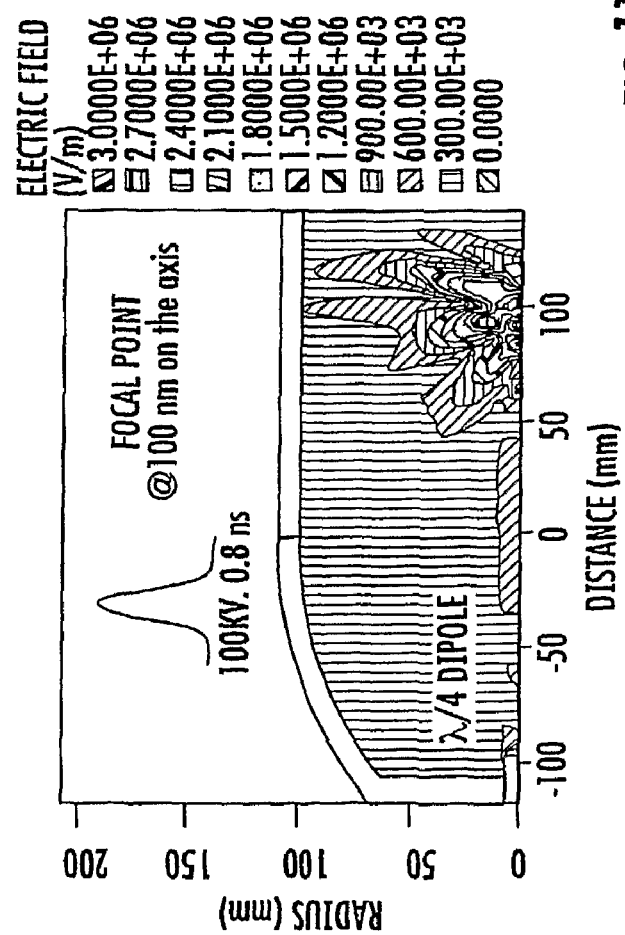
FIG. 17

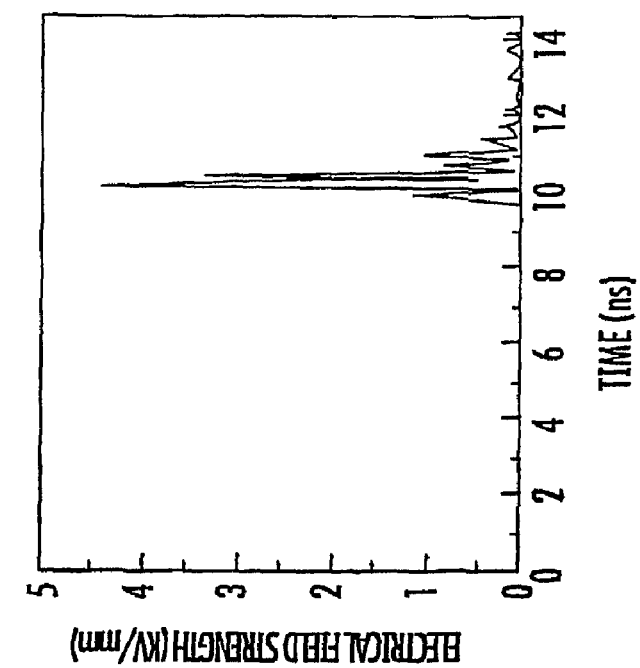
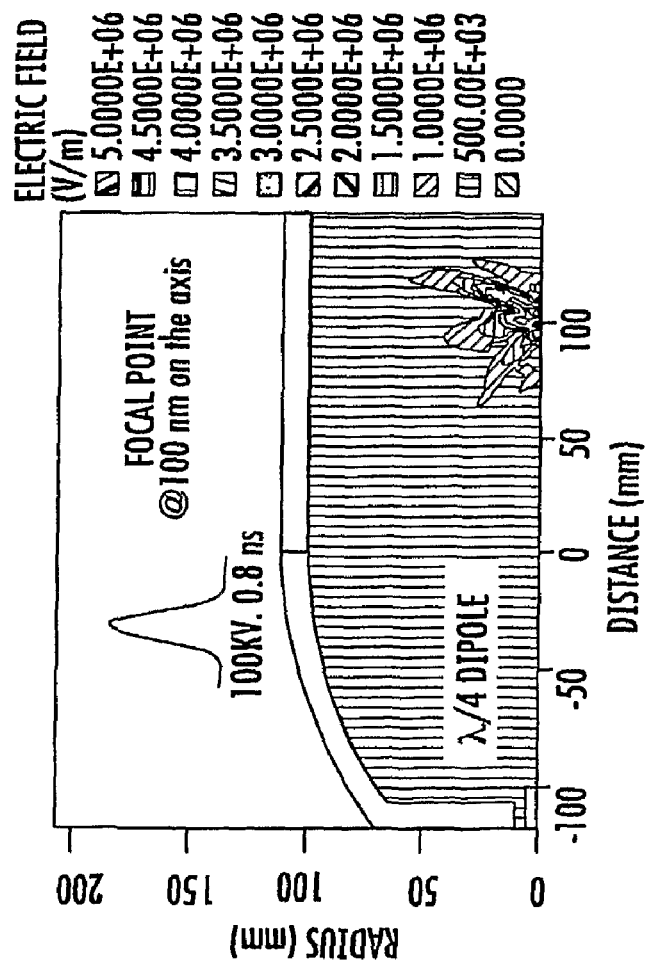
FIG. 13

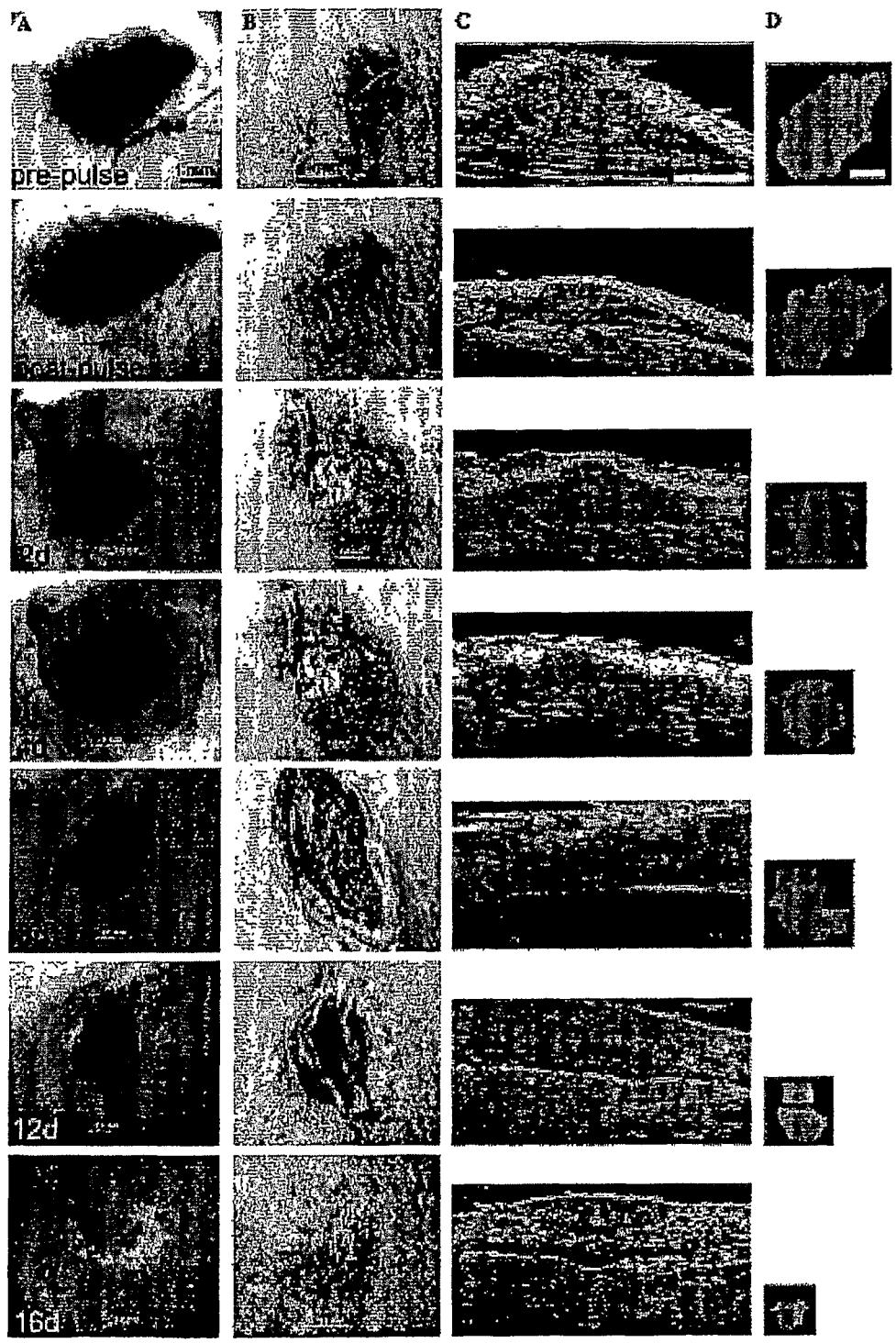
FIG. 20 A-D

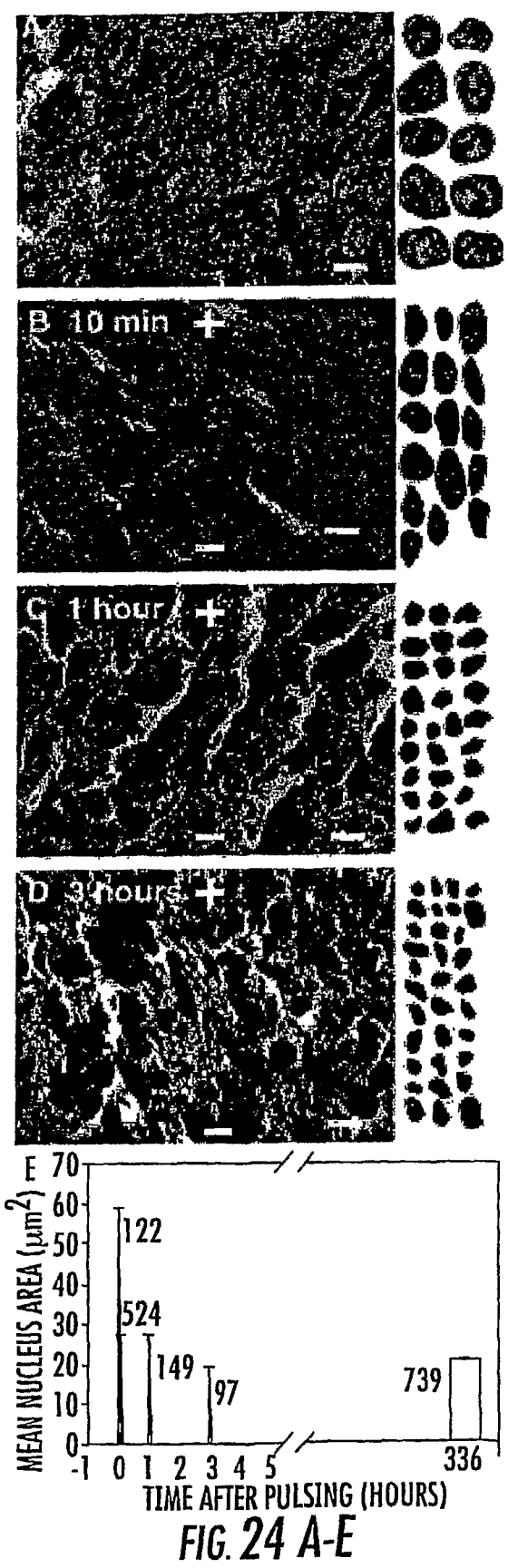
FIG. 24 A-E

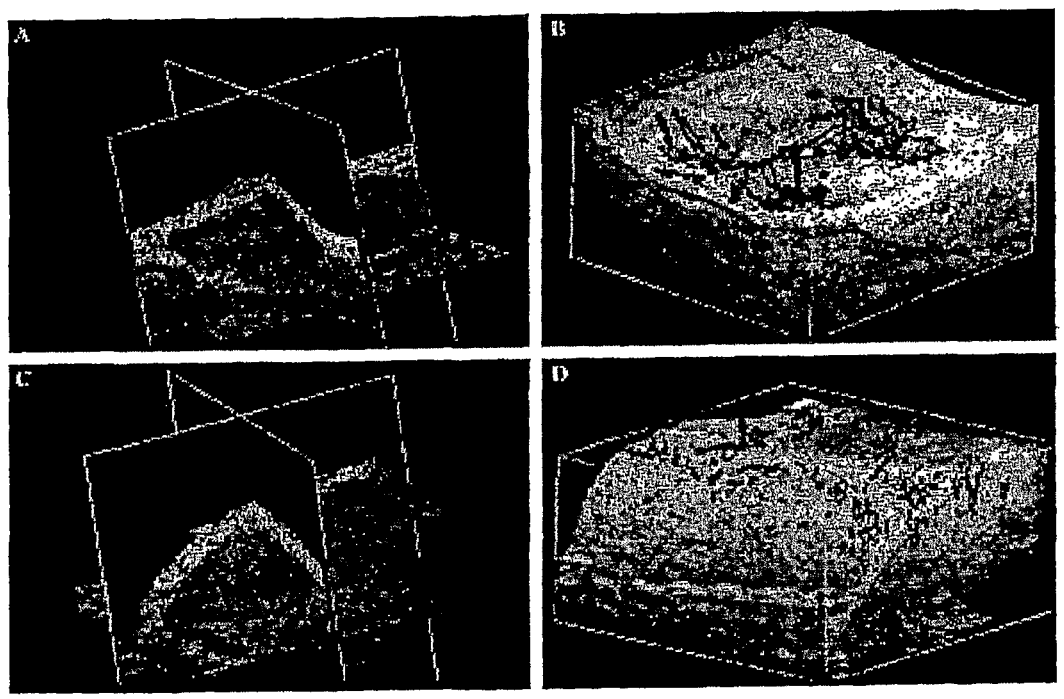
FIG. 25 A-D

ULTRAWIDEBAND ANTENNA FOR OPERATION IN TISSUE

CROSS-REFERENCE TO RELATED APPLICATIONS

This application is a §371 national stage entry of International Application No. PCT/US2006/032440, filed Aug. 21, 2006, which claims priority to U.S. Provisional Application No. 60/709,527, filed Aug. 19, 2005, and U.S. Provisional Application No. 60/800,729, filed May 16, 2006, all of which are hereby incorporated by reference.

FIELD OF THE INVENTION

A system that produces ultrashort electrical pulses is used for the treatment of cancer and other cellular and tissue disorders.

BACKGROUND

Cancer is one of the leading causes of disease, being responsible for 526,000 deaths in the United States each year. For example, breast cancer is the most common form of malignant disease among women in Western countries and, in the United States, is the most common cause of death among women between 40 and 55 years of age (Forrest, 1990). The incidence of breast cancer is increasing, especially in older women, but the cause of this increase is unknown. Malignant melanoma is another form of cancer whose incidence is increasing at a frightening rate, at least sixfold in the United States since 1945, and is the single most deadly of all skin diseases.

One of the most devastating aspects of cancer is the propensity of cells from malignant neoplasms to disseminate from their primary site to distant organs and develop into metastases. Despite advances in surgical treatment of primary neoplasms and aggressive therapies, most cancer patients die as a result of metastatic disease. Animal tests indicate that about 0.01% of circulating cancer cells from solid tumors establish successful metastatic colonies.

Electric fields have been employed in several different types of cancer therapy. Some of these involve radiofrequency or microwave devices that heat the tumor to greater than 43° C. to kill the cells via hyperthermia. Others use pulsed electric fields to permeabilize the tumor cells to allow the introduction of toxic drugs or DNA.

There is an urgent need in the art to treat cancer and other disorders without the use of invasive therapy and chemotherapeutic agents and with little or no effect on the whole animal. We have discovered that ultrashort electrical pulses can be used as a purely electrical cancer therapy that kills tumors and abnormal cells without hyperthermia or drugs.

SUMMARY

The invention is directed to an apparatus and methods of treating abnormal cells. The apparatus produces pulses or 10 picoseconds to 1 micro second (ultrashort pulses). A new domain of pulsed electric field interactions with cell structures and functions opens up when pulse duration is reduced to values such that the such that membrane charging becomes negligible. For mammalian cells this holds for pulse duration of one nanosecond and less. Instead of membrane charging, which leads to electroporation, direct electric fields interactions with the various parts of the cell with intensities determined by the complex dielectric constant will be with membranes because of the low dielectric constant compared to the cytoplasm.

In a preferred embodiment, wide band, intense non-ionizing radiation applied to cells and tissues as nanosecond pulses, nsPEFs have pulse durations (1-300 ns) and electric fields ($\leq 1$ MV/cm), with measured thermal changes being negligible. When the pulse duration is shorter than the dielectric relaxation time of the cytoplasm, nucleoplasm and surrounding media, a new temporal domain is opened for cell responses where electric fields act directly on molecules instead of charging membranes. When electric fields are sufficiently strong, they can cause conformation changes that can gate ion channels and mimic cell signaling.

For conventional electroporation pulses, which are generally on the order of tens of microseconds or milliseconds, effects on cells scale with the product of the pulse durations into the sub-microsecond range and increased the electric field. The nPEFs scale with the product of the pulse duration and the electric field. However, they are independent of the energy density. Both conventional electroporation and the nsPEF effects are due to membrane charging, but the outcomes on biological cells are distinctly different. When pulses are decreased, into the sub-nanosecond range, membrane charging is no longer possible because the pulses are so short that there is not time for the membranes to charge completely. Under these conditions the effects of sub-nanosecond pulses are likely due to direct effects on molecules.

The method includes a means to modify cell structures and functions by utilizing the dielectric properties of cells. Affected cell structures include but are not limited to the mitochondria, endoplasmic reticulum, nucleus, nucleolus, Golgi apparatus, DNA, RNA, messenger RNA, proteins, DNA-protein interactions, RNA-protein interactions, protein-protein interactions, amino acids, lipids, lipid rafts, and membrane receptors, including ion channels. Cell functions include, but are not limited to, metabolism, transcription, translation, gene expression, secretion, neurotransmitter release, ion channel gating, apoptosis, cell cycle regulation, second messenger generation, enzyme activities, reactive oxygen species generation, oxidation/reduction reactions. These actions can affect a wide range of cell structures, functions and reactions that have therapeutic or diagnostic applications.

In a preferred embodiment a system/apparatus generates monopolar, bipolar, and oscillatory high voltage pulses with amplitudes from 10 kV to 1 MV, and pulse durations (half periods) ranging from about 10 picoseconds (ps) to 50 nanoseconds (ns). In an preferred embodiment, the apparatus generates pulse durations (half periods) ranging from about 50 picoseconds (ps) to 5 nanoseconds (ns).

In another preferred embodiment, the system or apparatus focuses the energy of the electrical pulses into a well defined volume in cell cultures, tissues and organs using for example, an ellipsoidal antenna.

In another preferred embodiment, the system or apparatus emits the energy over a large distance, using for example, a parabolic antenna.

In another preferred embodiment, the apparatus or system delivers the electrical energy through a single or multiple coaxial cable or other waveguides to targets in tissue.

In a preferred embodiment, pulse durations are less than 1 nanosecond. Electric fields can be as high as 1.5 MV/cm.

In another preferred embodiment, the apparatus generates an electric pulse which induces apoptosis in cells and tissue. The cells are abnormal cells, such as for example, tumors, cells infected with a disease or tumor causing organism such as a virus. Other disease causing organisms include, bacteria, fungi, parasites and the like.

In another preferred embodiment, the apparatus generates an electric pulse which induces calcium or neurotransmitter release in cells. An example wherein the apparatus is important is in the treatment of depression or any neurological disorders where the neurotransmitters deviate from normal physiological levels.

Other applications include, but not limited to: mimicking hormones, enhancing gene expression, and inducing apoptosis in tumors and tissues. Pulsed electric field interactions with cell structures and functions allows for pulse durations that are reduced to values such that membrane charging becomes negligible. For mammalian cells, this holds for pulse durations of one nanosecond and less. Instead of membrane charging, which leads to electroporation, direct electric field interactions with the various part of the cell with intensities determined by the complex dielectric constant will dominate.

This approach will ultimately allow applications for pulsed electric fields without invasive electrode delivery, using antennas instead. A possible configuration, which allows us to generate very high electric fields using a focusing antenna, is discussed infra. With an almost closed ellipsoidal antenna and 0.4 ns pulses electric fields exceeding 100 kV/cm can be achieved in the target area with an applied antenna voltage of 100 kV. The application of higher voltage pulses will consequently allow us to generate electric fields of several 100 kV/cm in the focal area. This is sufficient to induce apoptosis by using multiple pulses. Using multiple pulses, we have shown apoptosis at much lower electric fields that required for single pulse operation.

Besides inducing apoptosis, inducing non-lethal effects such as calcium release from subcellular structures (Beebe S J, White J, Blackmore P F, Deng Y, Somers I L, Schoenbach K H. Diverse effects of nanosecond pulsed electric fields on cells and tissues. *DNA Cell Biol.* 2003 December; 22(12): 785-96; White J A, Blackmore P F, Schoenbach K H, Beebe S J. Stimulation of capacitative calcium entry in HL-60 cells by nanosecond pulsed electric fields. *J Biol Chem.* 2004 May 28; 279(22):22964-72; Beebe S J, Blackmore P F, White J, Joshi R P, Schoenbach K H. Nanosecond pulsed electric fields modulate cell function through intracellular signal transduction mechanisms. *Physiol Meas.* 2004 August; 25(4):1077-93; Buescher E S, and Schoenbach K H. Effects of submicrosecond, high intensity pulsed electric fields on living cells-intracellular electromanipulation. *IEEE Transactions on Dielectrics and Electrical Insulation* 2003, 10, 788-794; E. S. Buescher, R. R. Smith, K. H. Schoenbach, "Submicrosecond, intense pulsed electric field effects on intracellular free calcium: mechanism and effects," *IEEE Trans Plasma Science* 32, 1563-1572 (2004)), or neurotransmitter release can be an attractive application of this new method. Calcium is a key regulator of numerous cellular functions, and also influences cell signaling ((Beebe S J et al., *DNA Cell Biol.* 2003 December; 22(12):785-96; White J A et al, *J Biol Chem.* 2004 May 28; 279(22):22964-72; Beebe S J et al, *Physiol Meas.* 2004 August; 25(4):1077-93; Buescher E S, and Schoenbach K H. *IEEE Transactions on Dielectrics and Electrical Insulation* 2003, 10, 788-794; E. S. Buescher et al, *IEEE Trans Plasma Science* 32, 1563-1572 (2004)). This would, for example, have implications for electro-stimulation. Since the release of calcium has been shown to require much lower electric fields than apoptosis induction, the constraints oil pulse generator can be relaxed considerably. This may then even allow stimulating calcium-related functions over a longer distance, using parabolic, rather than ellipsoidal reflectors. In general, the use of subnanosecond pulses not only allows us to enter a new field of electric field-cell interactions, but might open the door to a range of therapeutic applications which require electromagnetic energy delivery into tissue not easily accessible by solid electrodes such as needles.

In another preferred embodiment, the apparatus or system modifies cell structures and functions by utilizing the dielectric properties of cells. Uses include treatment of metabolic disorders, regulating hormones, neurotransmitters etc. Affected cell structures include but are not limited to the mitochondria, endoplasmic reticulum, nucleus, nucleolus, Golgi apparatus, DNA, RNA, messenger RNA, proteins, DNA-protein interactions, RNA-protein interactions, protein-protein interactions, amino acids, lipids, lipid rafts, and membrane receptors, including ion channels. Cell functions include, but are not limited to, metabolism, transcription, translation, gene expression, secretion, neurotransmitter release, ion channel gating, apoptosis, cell cycle regulation, second messenger generation, enzyme activities, reactive oxygen species generation, oxidation/reduction reactions. These actions can affect a wide range of cell structures, functions, and reactions that have therapeutic or diagnostic applications.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIGS. 10-13 are graphs showing antenna configuration, the spatial distribution of the electric field in the target volume; and the temporal distribution of the electric field. The figures on the left show the antenna configuration and the spatial distribution of the electric field in the target volume; the figures on the right show the temporal distribution of the electric field in the target point. Parameters are antenna design (FIGS. 10 and 12 half ellipsoids, FIGS. 11 and 13 full ellipsoids) and the pulse duration (FIGS. 11 and 12, 0.8 ns, and FIGS. 12 and 13, 0.4 ns).

FIG. 16A is an example of a three hundred nanosecond pulse-forming network in Blumlein configuration. Width of each ceramic capacitor is 3 cm. FIG. 16B is a graph showing the typical voltage (red or solid trace) and current (blue or dashed trace) pulse generated across a tumor.

FIG. 17A is a scan of a photograph showing a 5-needle array used for the first experiments. FIG. 17B is a 3-D plot showing the electric field generated when 8 kV is placed on the center electrode and the outer four electrodes are held at ground.

FIGS. 18A-18T are scans of photographs showing a typical response of skin and melanoma to one or two applications of 100 pulses using a 5-needle array electrode on mouse #56. Each matched pair of photographs represents an in vivo transillumination of the skin on the left and a surface view on the right. Numbers on the far left indicate the number of days after pulsing at which all three matched pairs to the right were photographed. FIGS. 18A-18 show the typical response of normal skin to 100 pulses (300 ns long, 20 kV/cm, 0.5 Hz) delivered on day 0. Small superficial erosion in shown in FIG. 18B grows in (FIG. 18C-18E) and indicates loss of some or all epidermis. (FIG. 18H-18M) The electrode array was inserted into this tumor on day 0 but no pulses were delivered. (FIGS. 18O-18T) One hundred pulses (300 ns long, 20 kV/cm) were delivered at 0.5 Hz on day 0 and day 1. Necrosis evident on day two becomes more intense over time. Scale bars (FIGS. 18A-18T) 1 mm and all photographs in a given row are at the same magnification.

(FIGS. 19A, 19B) 4 kV was applied between center and outer needles spaced 4 mm apart to give an average field of 10 kV/cm. (FIGS. 19C-19E) Eight kilovolt was applied between the center and outer needles to give an average field of 20 kV/cm.

FIGS. 20A-20D are scans of photographs showing a typical response of a melanoma to three applications of 100 pulses (300 ns, 40 kV/cm, 0.5 Hz) 30 min apart on day 0 followed by a single application on day 4 using a 5 mm diameter parallel plate electrode on mouse #102. Collection of seven matched sets of images of the same tumor all taken on the day indicated in the lower left corner of the transillumination image. (FIG. 20A, (Column A)) shows the transillumination image. (FIG. 20B, (Column B)) Surface view. (FIG. 20 C, (Column C)) Ultrasound slice at center of tumor. (FIG. 20D, (Column D)) 3-D reconstruction made from 100 serial ultrasound slices through tumor. Magnification is constant for each column and scale bar at top of each column represents 1 mm.

FIG. 23A is a scan of a micrograph of a thermocouple made by fusing a copper wire with one made from constantine. FIG. 23B is a plot showing temperature recorded from a thermocouple positioned inside of a melanoma during pulse application. Lower dots indicate the time that each pulse was applied.

FIGS. 24A-24E show the targets and mechanisms of nsPEF effects. FIGS. 24A-24D are scans of photographs showing seven micrometer thick paraffin sections of control and treated melanomas fixed at the indicated time after treatment with 100 pulses (300 ns, 40 kV/cm, 0.5 Hz) stained with hematoxylin and eosin. The clearest nuclei were copied and placed to the right of each section to assist in size comparison. (FIG. 24A) Control tumor section; (FIG. 24B) 10 min post-treatment. (FIG. 24C) 1 h post-treatment. (FIG. 24D) Three hours post-treatment. Scale bars: 10 µm. FIG. 24E is a graph showing the mean nuclear area versus time after 100-200 pulses were applied. Number of cell nuclei measured from at least two mice for each time point indicated next to each column and bars represent SEM. Breakin time is 330 h. There is a significant difference between the 0 h prepulse control and all of the other time points ($p<0.001$) as well as between 1 and 3 h ($p<0.001$). There is no significant difference between 0.1 and 1 h. Scale bars in (A)-(D): 10 µm.

FIGS. 25A-25D show the blood flow in melanoma before and after nsPEF application. FIG. 25A shows the 3-D reconstruction of volume of melanoma; FIG. 25B shows the power Doppler reconstruction of blood flow before field application. FIG. 3C shows the 3-D reconstruction of volume of the same melanoma shown in FIG. 25A generated about 15 min after 100 pulses (300 ns, 40 kV/cm, 0.5 Hz). FIG. 25D shows the power Doppler reconstruction of blood flow in the same tumor shown in FIG. 25B generated about 15 min after 100 pulses (300 ns, 40 kV/cm, 0.5 Hz).

DETAILED DESCRIPTION

Figure 1A:
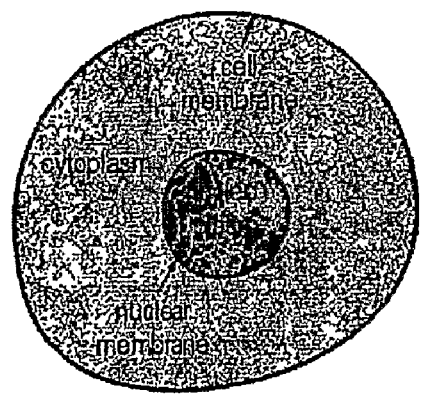
FIG. 1A is a schematic representation showing the structure of a biological cell (as would be seen with a light microscope).

Antenna Parameters: 1. Near Field Antenna (target very close to electromagnetic wave source). (a) In order to generate electric fields of this amplitude by antennas of reasonable size and power, cells, tissues were placed in the near field of the antenna. The near field is defined as the region bounded by a sphere with a radius of less than the wavelength divided by $2\pi$ (b) The spatial resolution for such near field "antennas" is determined by the electrode dimensions. In a coaxial cable which is used as catheter this would be the diameter of the center conductor and the distance to the surrounding, coaxial conductor. In a dual-coaxial "antenna, where the center conductor is surrounded by two coaxial cylinders where the inner coax-cable delivers one pulse, and the outer coax cable (determined by the two outer coaxial conductors) the second, phase shifted pulse the principle of superposition is used (for far-field applications, this principle is used in phased array antenna systems) to "focus" these fields in a limited spatial area. (c) In the dual-coax system focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

Antenna Parameters 2. Focusing Antenna (distance of target to source determined by the focusing device which can be either a lens or a reflector). a) In order to generate electric fields of this amplitude by antennas of reasonable size and power, cells, tissues were placed in the focal point volume of the antenna. The focal point volume is defined as the region bounded by a sphere with a radius on the order of the wavelength, centered at the focal point. (b) In order to focus these fields in a limited spatial area, focusing reflectors or lenses are used. (c) Focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

Definitions

In accordance with the present invention and as used herein, the following terms are defined with the following meanings, unless explicitly stated otherwise.

As used herein, "a", "an," and "the" include plural references unless the context clearly dictates otherwise.

As used herein, "cancer" refers to all types of cancer or neoplasm or malignant tumors found in mammals, including, but not limited to: leukemias, lymphomas, melanomas, carcinomas and sarcomas. Examples of cancers are cancer of the brain, breast, pancreas, cervix, colon, head & neck, kidney, lung, non-small cell lung, melanoma, mesothelioma, ovary, sarcoma, stomach, uterus and Medulloblastoma. The term "cancer" includes any cancer arising from a variety of chemical, physical, infectious organism cancer causing agents. For example, hepatitis B virus, hepatitis C virus, human papillomaviruses; sun; lead and lead compounds, X-rays, compounds found in grilled meats, and a host of substances used in textile dyes, paints and inks. Further details of cancer causing agents are listed in *The Report on Carcinogens*, Eleventh Edition. Federal law requires the Secretary of the Department of Health and Human Services to publish the report every two years.

Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

The term "sarcoma" generally refers to a tumor which is made up of a substance like the embryonic connective tissue and is generally composed of closely packed cells embedded in a fibrillar or homogeneous substance. Examples of sarcomas which can be treated with the compositions and optionally a potentiator and/or chemotherapeutic agent include, but not limited to a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the compositions and optionally a potentiator and/or another chemotherapeutic agent include but not limited to, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the compositions and optionally a potentiator and/or a chemotherapeutic agent include but not limited to, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

"Diagnostic" or "diagnosed" means identifying the presence or nature of a pathologic condition or a patient susceptible to a disease. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters, and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, the pulsed electric field can directly decrease the pathology of tumor cells, or render the tumor cells more susceptible to treatment by other therapeutic agents, e.g., radiation and/or chemotherapy.

The treatment of neoplastic disease, cancer, or neoplastic cells, refers to an amount of the electromagnetic or pulse energy delivered by the apparatus or system, described throughout the specification and in the Examples which follow, capable of invoking one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention of tumor cell infiltration into peripheral organs; (6) inhibition, including (i) reduction, (ii) slowing down or (iii) complete prevention of metastasis; (7) enhancement of anti-tumor immune response, which may result in (i) maintaining tumor size, (ii) reducing tumor size, (iii) slowing the growth of a tumor, (iv) reducing, slowing or preventing invasion or (v) reducing, slowing or preventing metastasis; and/or (8) relief, to some extent, of one or more symptoms associated with the disorder.

The terms "dosing" and "treatment" as used herein refer to any process, action, application, therapy or the like, wherein a subject, particularly a human being, is rendered medical aid with the object of improving the subject's condition, either directly or indirectly.

The treatment of a patient with the apparatus of the invention, can be combined with one or more therapies. For example, in the case of treating cancer, the patient may be treated with a combination of electric pulse fields and a regimen of chemotherapeutic agents. A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamticin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Treatment of an individual suffering from an infectious disease organism refers to a decrease and elimination of the disease organism from an individual. For example, a decrease of viral particles as measured by plaque forming units or other automated diagnostic methods such as ELISA etc.

"Neural (neuronal) defects, disorders or diseases" as used herein refers to any neurological disorder, including but not limited to neurodegenerative disorders (Parkinson's; Alzheimer's) or autoimmune disorders (multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bi-polarism, schizophrenia and the like; narcolepsy/sleep disorders (including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neuron disease, ataxias, muscular rigidity (spasticity) and temporomandibular joint dysfunction; Reward Deficiency Syndrome (RDS) behaviors in a subject; neurotoxicity caused by alcohol or substance abuse (e.g. ecstasy, methamphetamine, etc.).

As used herein, the term "infectious agent" or "infectious disease organism" or "disease organism" refers to all organism wherein growth/multiplication leads to pathogenic events in humans or animals. Examples of such agents are: bacteria, fungi, protozoa and viruses.

Apparatus/System

Intracellular electromanipulation requires electric fields on the order of 10 kV/cm to 300 kV/cm when 10 ns pulses are applied for single and multiple shot operation. The range in electric field strength reflects the range in effects: for low electric fields, we have observed nonlethal effects based on calcium release, for high electric fields, apoptosis has been achieved. This is the case for single-shot operation. For multiple-shot operation at 10 ns, the electric field could be reduced to values below 100 kV/cm, with apoptosis still being observed. Besides the electric field, the pulse duration plays an important role. Based on the results of experiments, any intracellular effect seems to scale with the product of pulse duration and electric field intensity. This means that any decrease in pulse duration needs to be compensated by an increase in electric field. For a 1 ns pulse, assuming multiple shot conditions, apoptosis would require electric fields close to 1 MV/cm. For a nonlethal effect such as calcium release (which in turn could have a number of secondary effects, such as platelet activation, neural stimulation, etc.), the required electric field would be lower, but probably still in the range of hundreds of kV/cm. These estimations are based on the assumption that the biological effects are determined by electrical charging of the plasma membrane and subcellular membranes. However, a new domain of pulsed electric field interactions with cell structures and functions opens up when the pulse duration is reduced to values such that membrane charging becomes negligible. For mammalian cells, this holds for pulse durations of one nanosecond and less. Instead of membrane charging, which leads to electroporation, or in the case of ultrashort pulses to nanoporation, direct electric field interactions with the various parts of the cell with intensities determined by the complex dielectric constant will dominate. Besides entering a new domain of electric field-cell interactions, this new approach will ultimately allow applications for pulsed electric fields without invasive electrode delivery, using antennas instead.

Antenna Parameters: 1. Near Field Antenna (target very close to electromagnetic wave source). (a) In order to generate electric fields of this amplitude by antennas of reasonable size and power, cells, tissues were placed in the near field of the antenna. The near field is defined as the region bounded by a sphere with a radius of less than the wavelength divided by $2\pi$. (b) The spatial resolution for such near field "antennas" is determined by the electrode dimensions. In a coaxial cable which is used as catheter this would be the diameter of the center conductor and the distance to the surrounding, coaxial conductor. In a dual-coaxial "antenna, where the center conductor is surrounded by two coaxial cylinders where the inner coax-cable delivers one pulse, and the outer coax cable (determined by the two outer coaxial conductors) the second, phase shifted pulse the principle of superposition is used (for far-field applications, this principle is used in phased array antenna systems) to "focus" these fields in a limited spatial area. (c) In the dual-coax system focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

Antenna Parameters 2. Focusing Antenna (distance of target to source determined by the focusing device which can be either a lens or a reflector). a) In order to generate electric fields of this amplitude by antennas of reasonable size and power, cells, tissues were placed in the focal point volume of the antenna. The focal point volume is defined as the region bounded by a sphere with a radius on the order of the wavelength, centered at the focal point. (b) In order to focus these fields in a limited spatial area, focusing reflectors or lenses are used. (c) Focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

In a preferred embodiment, a dual coax antenna can be used, where the two waves can be phase-shifted to achieve highest fields where needed. Modeling results using an existing code, "MAGIC®", indicate that this approach is successful.

Measurements of the electric field distribution in water, resembling the electrical properties of tissue, will be performed using the Kerr effect. A Mach-Zehnder interferometer is available and has been tested in evaluating water discharges.

In preferred embodiments, the invention comprises: a high voltage (up to 2 MV) ns pulse generator; designing and constructing a dual coax antenna; modeling the electric field distribution in tissue, dependent on a phase shift between the two coaxial waves, and measuring the electric field distribution in water using the Kerr effect.

In a preferred embodiment, the electric field pulse generator and/or electric pulse radiator (emitter) comprises electrodes, antennae, cables, coaxial cables, plates, and radiating fins.

In an another preferred embodiment, the antenna(e), e.g. the focusing antenna, comprise an ellipsoidal reflector, a parabolic reflector. Particularly preferred, the antenna comprises a focusing lens to allow for focusing the electric pulses. We have shown that the spatial resolution of the field is excellent and can be focused to a confined desired area, for example, from about 0.1 mm. This is particularly useful when focusing on, for example, a tumor without affecting the surrounding normal cells. The field can be expanded to include surrounding cells and tissues if desired. The lens can be made of any reflecting material or material which focuses the pulses, such, as for example, metal, plastic, glass, crystal and the like.

At high frequencies, lens antennas can be used to perform functions similar to reflector antennas. Both lenses and parabolic reflectors use free space as a feed network to excite a large aperture. The feed of a lens remains out of the aperture, eliminating aperture blockage and the resulting high sidelobe levels. Dielectric lens antennas are similar to the optical lens and the aperture of the antenna is equal to the projection of the rim shape. Lenses are divided into two categories single-surface and dual-surface. In the single-surface lens, one surface is an equiphase surface of the incident or emergent wave and the rays pass through normal to this surface without refraction.

In a dual-surface lens, refraction occurs at both lens surfaces. Single-surface lenses convert either cylindrical or spherical waves to plane waves. Cylindrical waves require a line source and a cylindrical lens surface, and spherical waves use a point source and a spherical lens surface. The far-field pattern is determined by diffraction from the aperture. Dual-surface lenses allow more control of the pattern characteristics. Both surfaces are used for focusing, and the second surface can be used to control the distribution in the aperture plane.

These simple lenses are many wavelengths thick, if their focal length and aperture are large compared to a wavelength m this case, the surface of the lens can be zoned by removing multiples of wavelengths from the thickness. The zoning can be done either in the refracting or nonrefracting surface. The zoned lens is frequency sensitive and can give rise to shadowing losses at transition regions.

Artificial dielectric lenses in which particles such as metal spheres, strips, disks, or rods can be introduced in the dielectric. The size of the particles has to be small compared to the wavelength. Metal plate lenses using spaced conducting plates are used at microwave frequencies. Since the index of refraction of a metal plate medium depends on the ratio of wavelength to the spacing between the plates, these lenses are frequency sensitive. The Luneberg lens is a spherical symmetric lens with an index of refraction that varies as a function of the radius. A plane wave incident on this lens will be brought to a focus on the opposite side. These lenses can be made using a series of concentric spherical shells, each having a dielectric constant.

Figure 5:
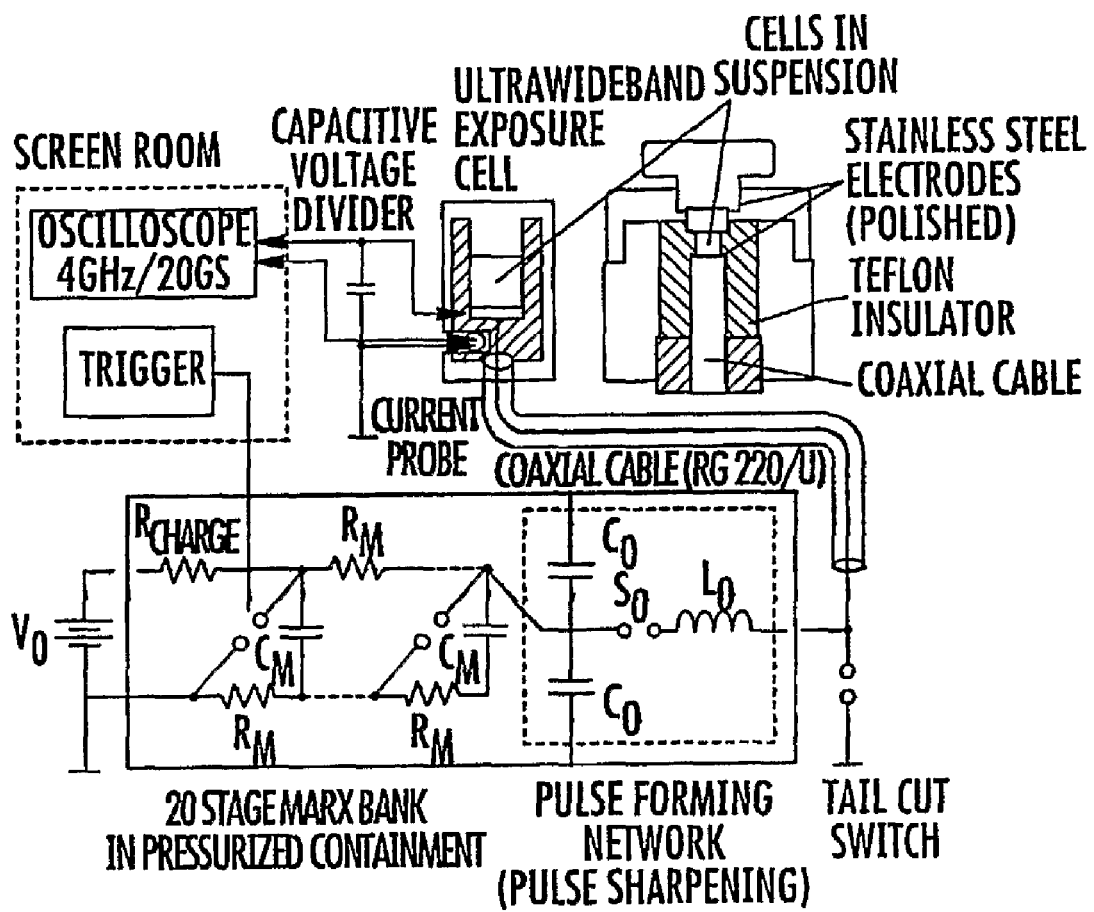
FIG. 5 is a schematic representation showing one embodiment of the apparatus. The figure shows a block diagram of ultrashort pulse generator with cross-section of exposure system (upper right).
Figure 14:
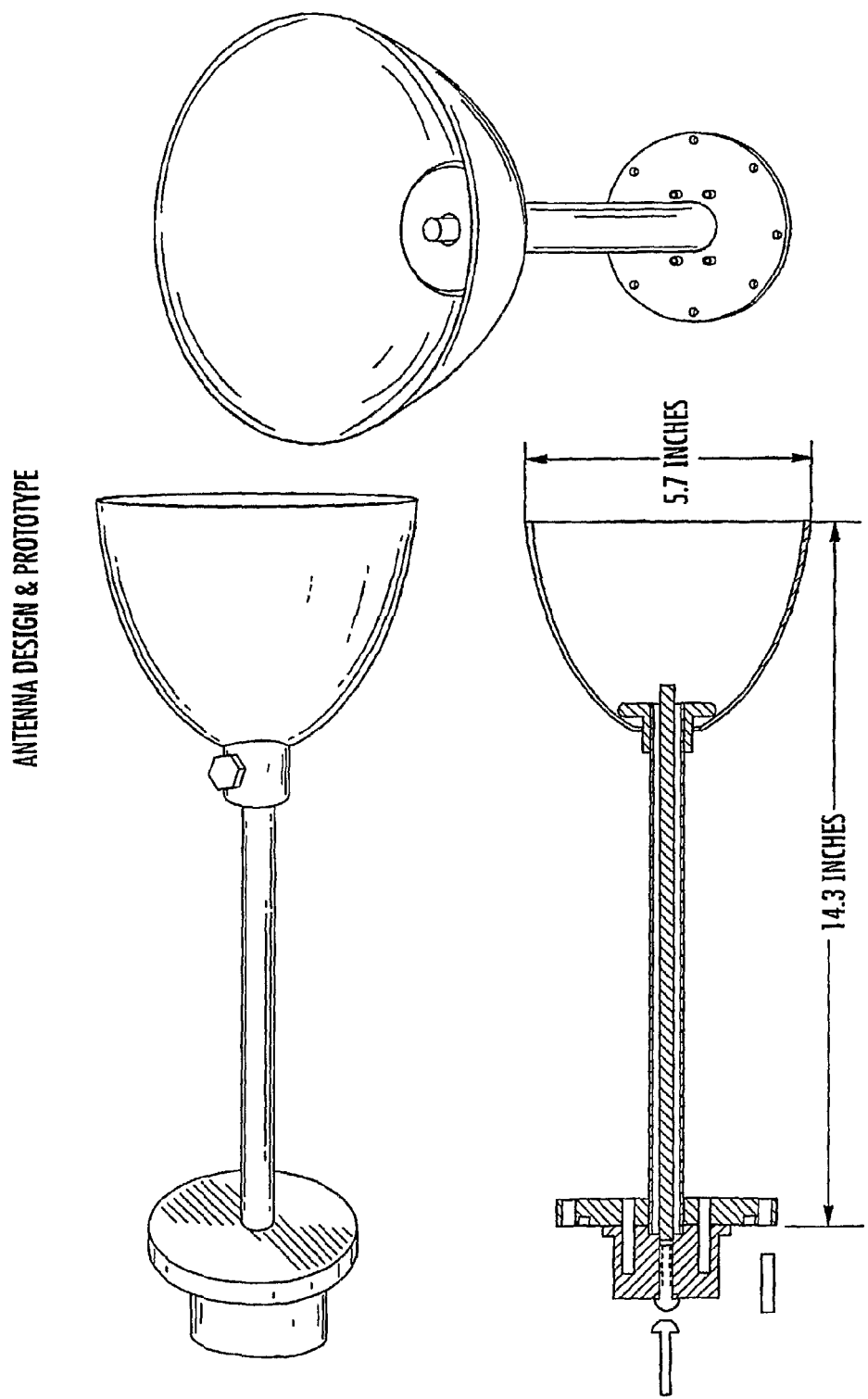
FIG. 14 is an illustration of an ellipsoid antenna with a reflecting surface.
Figure 15:
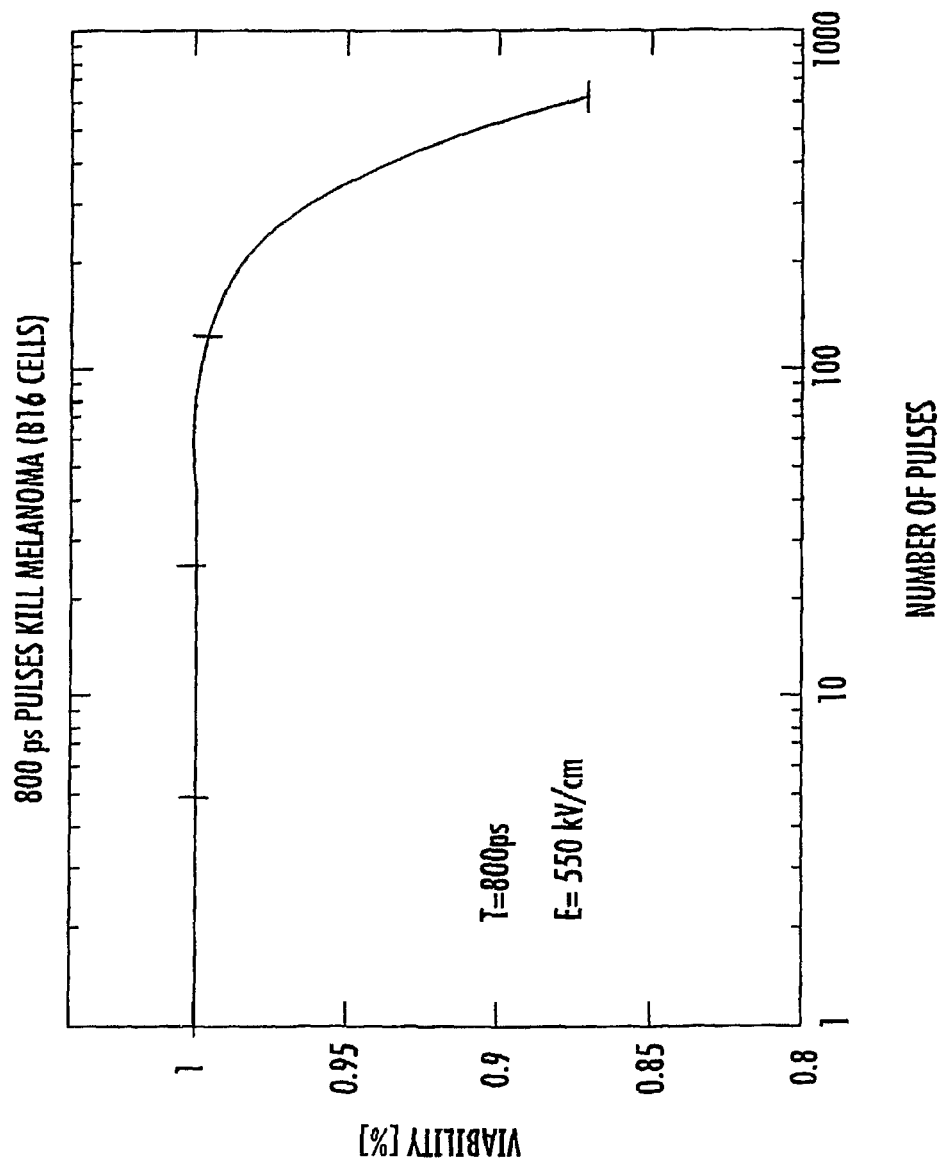
FIG. 15 is a graph showing 800 picosecond pulses kill melanoma cells.

An example for an ultrawideband antenna with focusing ellipsoidal reflector is shown in FIG. 14. The high voltage pulse which, in our case, is generated by means of a system as shown in FIG. 5. The voltage can be generated using generators known to one of ordinary skill in the field of pulsed power technology with a different pulse power system. The high voltage pulse is fed into a wire-antenna (dipole-antenna) through a high voltage coaxial cable. The dipole is located in one of the focal points of the ellipsoidal reflector. Consequently, the reflected wave is in such a configuration, reflected into the second focal point (focal volume) of the ellipsoid. In a therapeutic application, the target (e.g. a tumor inside a body) would be placed right at the second focal point. The effect on the tissue in front (e.g. at the skin) and behind the tumor would be less invasive, because the electrical energy density there would be smaller. Particularly, if the desirable effect (e.g. killing of tumor cells) is nonlinear, that means increases more than linearly with electric field above a certain threshold in electric field strength, the effect could be rather well confined to the desired treatment volume.

In other preferred embodiments, using pulses from 10 picoseconds to 1 microsecond (nsPEF) include pulses that are less than 1 nanosecond (Ultrashort pulses). A new domain of pulsed electric field interactions with cell structures and functions opens up when the pulse duration is reduced to values such that membrane charging becomes negligible. For mammalian cells, this holds for pulse durations of one nanosecond and less. Instead of membrane charging, which leads to electroporation, direct electric field interactions with the various part of the cell with intensities determined by the complex dielectric constant will dominate. Still, much of the interaction will be with membranes because of the low dielectric constant compared to the cytoplasm.

Besides entering a new domain of electric field-cell interactions, this new approach will ultimately allow applications for pulsed electric fields without invasive electrode delivery, using antennas instead. A possible configuration, which allows us to generate very high electric fields using a focusing antenna, has been introduced. Instead of a focusing antenna of the reflector type, it is also possible to use lenses to focus the electromagnetic energy into the tissue.

The advantages of the invention are numerous. Previously, we used wideband, intense non-ionizing radiation applied to cells and tissues as nanosecond pulsed electric fields (nsPEFs). Compared to conventional electroporation pulses, nsPEFs have shorter pulse durations (1-300 ns) and higher electric fields ($\leq 1$ MV/cm), which are so short that measured thermal changes are negligible. When the pulse duration is shorter than the dielectric relaxation time of the cytoplasm, nucleoplasm, and surrounding media, a new temporal domain is opened for cell responses where electric fields act directly on molecules instead of charging membranes. When electric fields are sufficiently strong, they can cause conformation changes that can gate ion channels and mimic cell signaling.

For conventional electroporation pulses, which are generally on the order of tens of microseconds or milliseconds, effects on cells scale with the product of the pulse duration, electric field, and energy density. Previously, we decreased pulse durations into the sub-microsecond range and increased the electric field. The nsPEFs scale with the product of the pulse duration and the electric field. However, they are independent of the energy density. Both conventional electroporation and nsPEF effects are due to membrane charging, but the outcomes on biological cells are distinctly different. When pulses are decreased into the sub-nanosecond range, membrane charging is no longer allowed because the pulses are so short that there is not time for the membranes to charge completely. Under these conditions the effects of sub-nanosecond pulses are likely due to direct effects on molecules. This is where physics meets biology head on and a new paradigm of mechanisms and effects occur on molecular structures and functions. This method includes a means to modify cell structures and functions by utilizing the dielectric properties of cells. Affected cell structures include but are not limited to the mitochondria, endoplasmic reticulum, nucleus, nucleolus, Golgi apparatus, DNA, RNA, messenger RNA, proteins, DNA-protein interactions, RNA-protein interactions, protein-protein interactions, amino acids, lipids, lipid rafts, and membrane receptors, including ion channels. Cell functions include, but are not limited to, metabolism, transcription, translation, gene expression, secretion, neurotransmitter release, ion channel gating, apoptosis, cell cycle regulation, second messenger generation, enzyme activities, reactive oxygen species generation, oxidation/reduction reactions. These actions can affect a wide range of cell structures, functions, and reactions that can have therapeutic or diagnostic applications.

The conditions include pulse durations are less than 1 nanosecond. Electric fields can be as high as 1.5 or 2 MV/cm. Experimental data indicate caspase activation without cell death. In addition to their well characterized role in apoptotic cell death, caspases are known to be involved in cell survival functions such as platelet activation, which is important for limiting blood loss during injury and wound healing, T-cell function and proliferation, and muscle cell differentiation.

This invention overcomes difficulties seen with the breakdown of the electric field in current pulse generators. This can be limited by limiting the electric field intensity. With present pulse generators, breakdown ranges are greater than 1.5 MV/cm. Thus, there is an upper limit to the electric fields that can be applied. Decreasing the pulse duration can extend this. Other engineering modification can be made, especially with in vitro and in vivo studies.

In order to explore the new regime in bioelectrics, the characteristic parameters of the electrical pulses need to be on the order of or less than the relaxation time of the cytoplasm, nucleoplasm, and the supernatant. This is a value of less than one nanosecond. A pulsed power system, which is able to provide subnanosecond pulses to a biological load, has been designed and built. The advantage of this sparkgap-switched pulsed power device is the high voltage, low impedance, and relatively low cost. The disadvantage is the restricted repetition rate. Whereas semiconductor opening switch-based pulsed power generators can operate at rep-rates of up to 50 kHz in a burst mode, sparkgap switch-based systems are generally restricted to approximately 100 Hz.

The block diagram of the experimental system is shown in FIG. 5, including the cross-section of the exposure system. An illustrative example of the system is shown in FIG. 5. The system comprises an electric field pulse generator. The generator comprises a means of generating the pulses. These can include without limitation, antennae, electrodes and the like. The electrodes 101 comprise any electric conducting materials such as stainless steel, carbon, carbon plate electrodes, copper, activated carbon impregnated with aluminum, titanium, tantalum, nickel. The activated carbon comprises, for example, acetylene black and KETJEN BLACK, natural graphite, thermal expansion graphite, carbon fibers, ruthenium oxide, titanium oxide, and the like. The electrodes can be coated with a coating material, such as for example, conductive agar. Preferably, the electrodes can be coated with conductive agar with a layer of about 0.001 mm to about 2 mm. Preferably, the coating of conductive agar is 1 mm.

The ultrashort pulse generator further comprises one or more receptacles 102 for the cells to be exposed to the ultrashort pulses, an insulator 103, a coaxial cable 104, an ultrawideband exposure cell 105, a current probe 106, a capacitive voltage divider 107, a screen room 108 comprising an oscilloscope 109 and trigger 110, a Marx-Bank with about 20 to 30 stages in a pressurized containment 111, a pulse forming or pulse sharpening network 112, and a tail cut switch 113. The system is not limited to the system shown in FIG. 5 which is a schematic illustration and not meant to limit or construe the invention in any way. The insulator can be comprised of any insulating material known to one of skill in the art, such as for example, TEFLON™. An example of a Marx-Bank is described by Carey, W. J and Mayes J. R. (2003) "Marx Generator Design and Performance." *Proc. Modulator Conf.* 2003, p. 625, incorporated herein in its entirety by reference.

Figure 6:
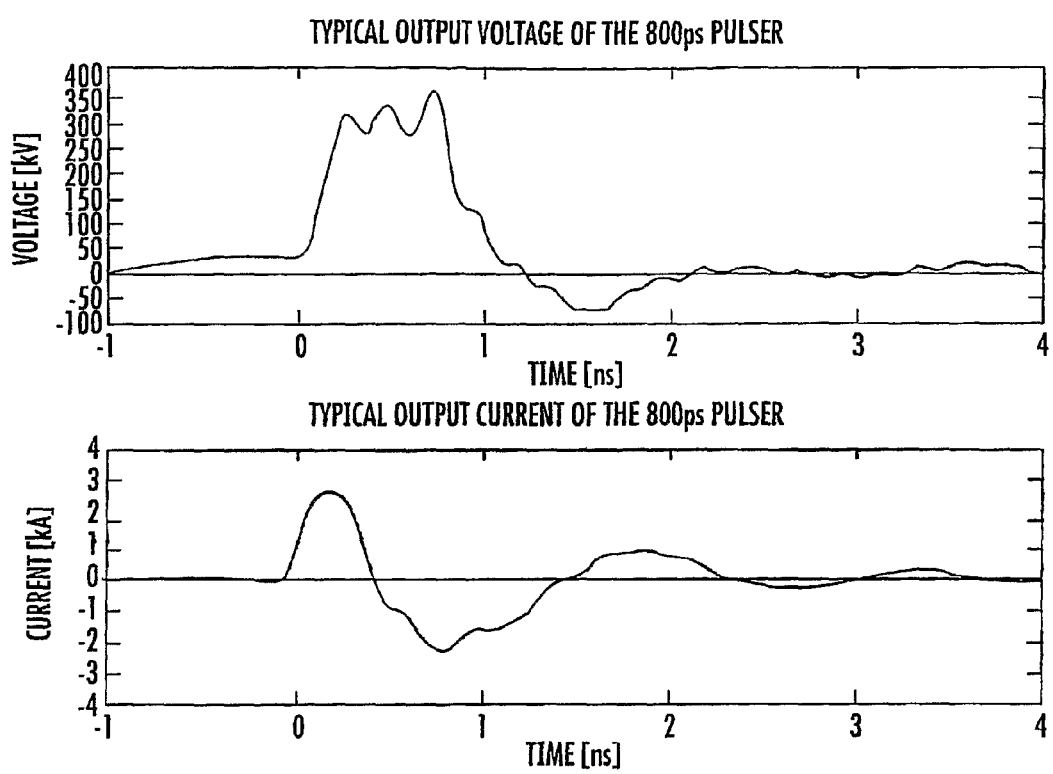
FIG. 6 is a graph showing voltage (upper part) and current (lower part) measured at the load, a suspension containing biological cells.

The system is able to generate 0.8 ns voltage pulses with an amplitude of 350 kV into a 50Ω load. Voltages measured at the high impedance load reach values of 700 kV. With a gap distance of 4.25 mm, this corresponds to electric fields of 1.5 MV/cm. A voltage and current pulse shape is shown in FIG. 6. In spite of this extremely large field, no electrical breakdown was observed. This is in line with results obtained with 200 and 400 ns pulses, where the breakdown field for water reached these values in a pin-plate electrode configuration. With pulse durations reduced by two orders of magnitude compared to those used in the water breakdown experiments, even multi-MV/cm fields in the subnanosecond range don't lead to breakdown.

In another preferred embodiment, the pulse generator comprises an antenna. Antenna Parameters: 1. Near Field Antenna (target very close to electromagnetic wave source). (a) In order to generate electric fields of this amplitude by antennas of reasonable size and power, cells, tissues were placed in the near field of the antenna. The near field is defined as the region bounded by a sphere with a radius of less than the wavelength divided by $2\pi$. (b) The spatial resolution for such near field "antennas" is determined by the electrode dimensions. In a coaxial cable which is used as catheter this would be the diameter of the center conductor and the distance to the surrounding, coaxial conductor. In a dual-coaxial "antenna," where the center conductor is surrounded by two coaxial cylinders where the inner coax-cable delivers one pulse, and the outer coax cable (determined by the two outer coaxial conductors) the second, phase shifted pulse the principle of superposition is used (for far-field applications, this principle is used in phased array antenna systems) to "focus" these fields in a limited spatial area. (c) In the dual-coax system focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

Antenna Parameters 2. Focusing Antenna (distance of target to source determined by the focusing device which can be either a lens or a reflector). a) In order to generate electric fields of this amplitude by antennas of reasonable size and power, cells, tissues were placed in the focal point volume of the antenna. The focal point volume is defined as the region bounded by a sphere with a radius on the order of the wavelength, centered at the focal point. (b) In order to focus these fields in a limited spatial area, focusing reflectors or lenses are used. (c) Focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

In another preferred embodiment, the apparatus of the system is a portable instrument. The uses of such an instrument are many. For example, treating a patient at a scene of an accident to relive pain, treatment of wounded soldiers on a field and the like.

Applications

In a preferred embodiment, a patient suffering from cancer is treated with the apparatus of the invention. The apparatus comprises an electric field pulse generator and/or electric pulse radiator (emitter) comprises electrodes, antennae, cables, coaxial cables, plates, and radiating fins. For whole body treatment the patient is exposed to the electric field in a cylinder, similar to MRI and the like. The field can be concentrated or focused in certain areas where the patient has solid tumors using a reflector and/or focusing lens. Wide field dispersal of the electric pulse is achieved using a parabolic reflector and or a combination of parabolic and ellipsoidal reflector, optionally combined with a focusing lens.

The electric field pulses can be adapted to each individual patients need, such as for example, varying the nsPEFs to include ultrashort pulses, e.g. 1 nanosecond and the field strength can vary. The treatment can cycle through ultrashort nsPEFs ranging from 1 picosecond to seconds and longer if need be. The intensity of the electric field can also vary from values on the order of V/cm up to MV/cm.

In another preferred embodiment, patients suffering from localized tumors, abnormal tissues, etc., e.g. melanoma, benign tumors, early stage cancer and the like are treated by focusing the electric field pulses on the area of the tumor. If a tumor is internal, the apparatus provides for delivery of the electric pulses to specific cells and/or tissues using, for example, cables, electrodes, etc.

In another preferred embodiment, cell cultures, tissues and organs are treated by focusing the electric field pulses on the area containing these cells. For example, the apparatus comprises a cell or tissue containment area.

Figure 8:
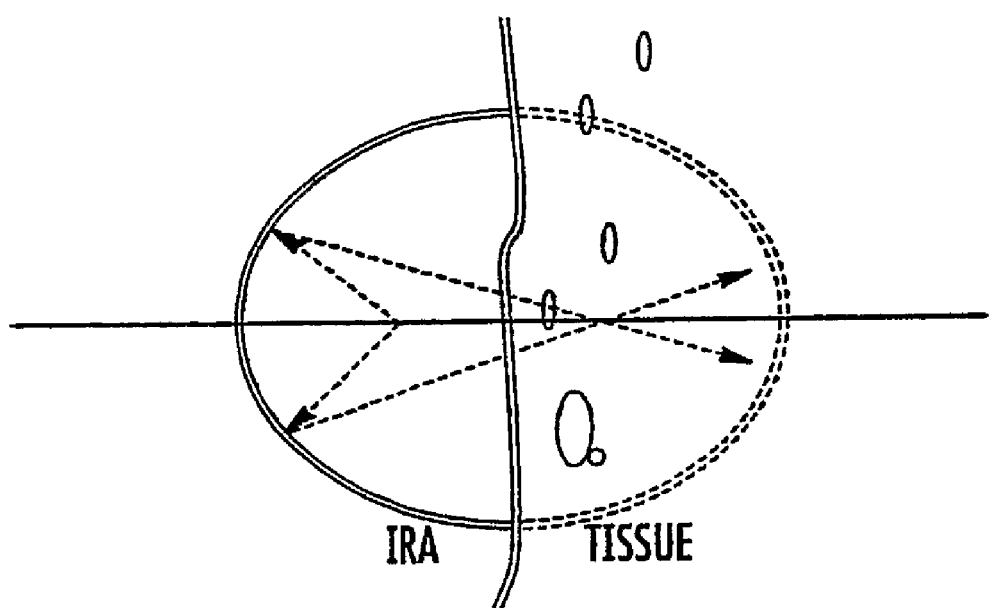
FIG. 8 is a schematic illustration showing schematics of focusing antenna (left) delivering electromagnetic energy to a focal point in tissue (right).
Figure 9A:
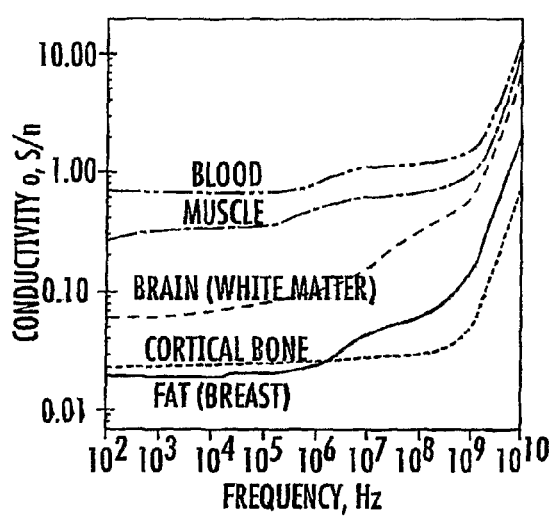
FIGS. 9A and 9B are graphs showing conductivity (FIG. 9A) and permittivity (FIG. 9B) of various tissues versus frequency.

In another preferred embodiment, abnormal, e.g. cells infected with a disease agent, physiologically imbalanced, pre-cancerous etc, or cancer cells are induced to undergo apoptosis by subjecting the cells to electric field pulses. The field can be focused on the cells using for example, an ellipsoid antenna. The apparatus allows for production of very high electric fields in restricted volumes is based on a geometrical concept: The power radiated from a point source located in one focal point of an ellipsoidal reflector is focused in the second focal point. This concept, and its application to focusing the electromagnetic energy in a small volume inside a tissue, is illustrated in FIG. 8. The source is located in the focal point of the ellipsoidal reflector on the left side. The electromagnetic waves reflected from the reflector are focused in the second focal point (right side) that is located in tissue. In order to reduce reflections at the tissue surface, the complex permittivity of the medium filling the space outside the tissue will be of approximately the same value as that of the tissue. Examples for tissue values are given in FIGS. 9A an 9B. Table 1 also shows electrical parameters of biological cells as measured using time domain dielectric spectroscopy. Permittivities in the 1 ns range (fundamental frequency approximately 100 MHz to 1 GHz) are in between 10 and 100. Conductivities vary between 0.02 to 1 S/m.

The observed apoptotic effects of a single pulse in the subnanosecond time range will open the possibility of using such pulses for therapies where apoptosis induction is important: in all types of removal of unwanted cells and tissue, particularly tumors. Studies of such effects are now being performed using electrodes as pulse delivery systems to the cell suspension or tissue [10]. For therapeutic applications, however, the use of electrodes, such as needles or plates, restricts the pulsed electric field method to treatment of tissue close to the body surface. The use of antennas, on the other hand, would allow one to apply such electric fields to tissues (tumors) that are not easily accessible with needles. Also, the focusing of electrical energy on the target would reduce the damage to the skin and normal tissue layers surrounding the target.

In this respect, the use of subnanosecond pulses does not only allow us to extend the pulsed field interactions with biological cells into a new type of time domain, as described infra, but makes it possible to use ultrawideband antennas to deliver these pulses to targets within the body. The ultrashort pulse duration, which defines the possible spatial resolution for such pulses, can be brought into a range that allows the targeting of specific parts of the body. For a 0.8 ns wide pulse, the cut-off frequency is approximately 0.75 GHz. Therefore, the wavelength corresponding to the cut-off frequency in tissue with a dielectric constant of 80 is approximately 5 cm, a value which determines the spatial resolution for such a pulse in tissue.

In another preferred embodiment, the antennae comprise an ellipsoidal reflector and/or a parabolic reflector. The pulses can be focused onto an area of interest, e.g. abnormal or tumor cells, tissues and the like, using an antenna which contains a focusing lens.

In another preferred embodiment, the apparatus is used on adipose tissue in order to "dissolve" excess adipose.

In another preferred embodiment, the apparatus produces electric fields for regulating hormone imbalances, treatment of metabolic disorders, neurotransmitter release, treatment of pain and the like. The electric field pulses have been shown for example, to affect calcium release which is known to regulate many cellular functions.

In one aspect, the patient suffering from thyroid disorders can be treated using the pulse fields as described herein. The target organ can be the thyroid.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

Figure 1B:
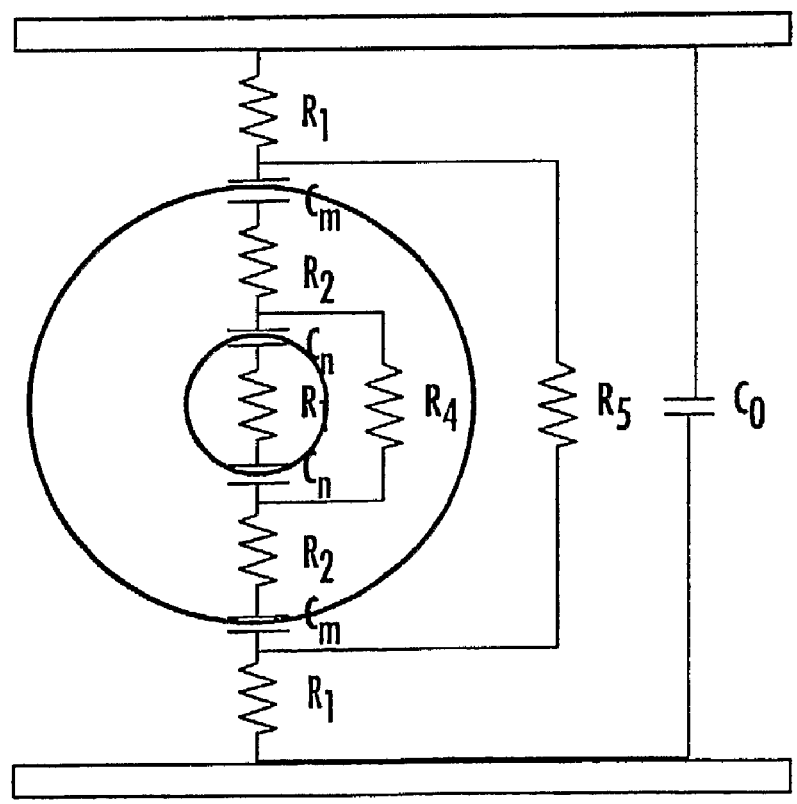
FIG. 1B is a schematic representation showing a double shell model of a biological cell, and superimposed equivalent circuit of the cell.

Method and Apparatus for Cellular and Intracellular Manipulation of Cell Functions with Ultrashort Electrical Pulses and for Targeted Delivery of the Electrical Pulses into Cell Cultures and Tissues. The effect of nanosecond electrical pulses of high intensity on biological cells and tissue has received considerable attention by the scientific community, particularly in the past five years, and has led to the establishment of a new research field: bioelectrics [1]. In this time domain, the rise time of the pulse is faster than the charging time of the plasma membrane, meaning that the field will pass through the membrane into the cytoplasm. This effect can be understood qualitatively by considering the cell as an electrical circuit, describing the various cell membranes by their capacitances, and the cytoplasm, which they enclose, by its resistance. FIG. 1A shows the cross-section of a mammalian cell, with the only membrane-bound substructure shown being the nucleus. The cytoplasm, which fills much of the cell, contains dissolved proteins, electrolytes and glucose and is moderately conductive as are the nucleoplasm and the cytoplasm in other organelles. On the other hand, the membranes that surround the cell and subcellular structures, have a low conductivity. We can therefore think of the cell as a conductor surrounded by an ideally insulating envelope, and containing substructures with similar properties. The equivalent circuit of such a cell (which is, for modeling purposes, considered as spherical) with one substructure, the nucleus, is shown in FIG. 1B.

If direct current electric fields or pulses of long duration (compared to the charging time of the capacitor formed by the outer membrane) are applied, eventually, only the outer membrane will be charged; the electric field generated across subcellular membranes during the charging will be zero for an ideal, fully insulating outer membrane. However, during the charging time of the outer membrane, we will also expect potential differences to be generated across subcellular membranes, an effect which will be stronger the shorter the pulse rise time is. Such charging times are in the submicrosecond range for human cells.

If the field is sufficiently large, it can have strong effects on intracellular organelles. Nanoseconds to hundreds of nanoseconds long, high voltage pulses have been shown to penetrate into living cells to permeabilize intracellular organelles [2,3] and release $Ca^{2+}$ from the endoplasmic reticulum [4,5,6]. They provide a new approach for physically targeting intracellular organelles with many applications, including precise control of apoptosis [7,8] and enhancement of gene transfection efficiency [8,9]. We also show that such pulsed electric fields cause shrinkage and even complete elimination of melanoma tumors [See, Example 3].

Figure 2:
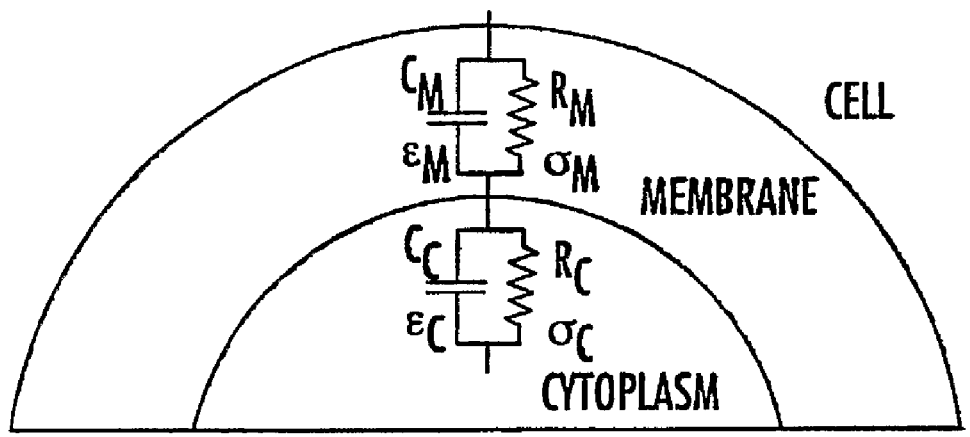
FIG. 2 is a schematic representation showing the equivalent circuit of a biological cell (single shell approximation).

From Submicrosecond Pulses to Subnanosecond Pulses: Entering a New Domain of Field-Cell Interactions: In the equivalent circuit shown in FIG. 1B, the conductance of the membranes is assumed to be zero, and the capacitive components of cytoplasm and nucleoplasm are neglected. The temporal range is determined by the dielectric relaxation times of membrane and cytoplasm and nucleoplasm, respectively. For simplicity, in the following discussion we will focus on a single shell model of a biological cell, which means that the effects on internal membrane-bound structures will not be considered. (The equivalent circuit for this case is shown in FIG. 2). However, it will be shown that the same conclusions that can be drawn from the discussion of the single shell model can easily be extended to predict electrical effects on the inner cell structures.

Figure 3:
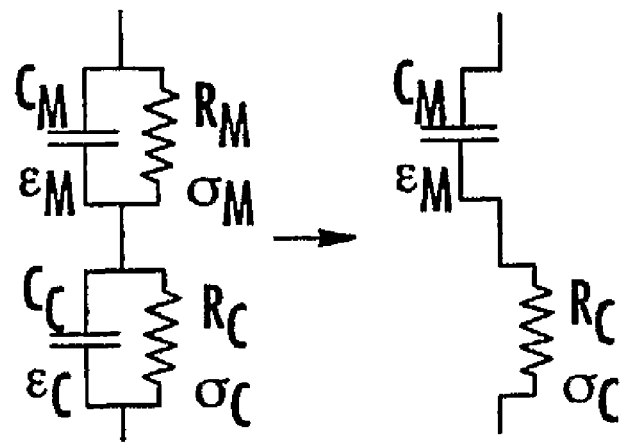
FIG. 3 is a schematic representation showing the equivalent circuit used to describe electroporation processes.
Figure 4:
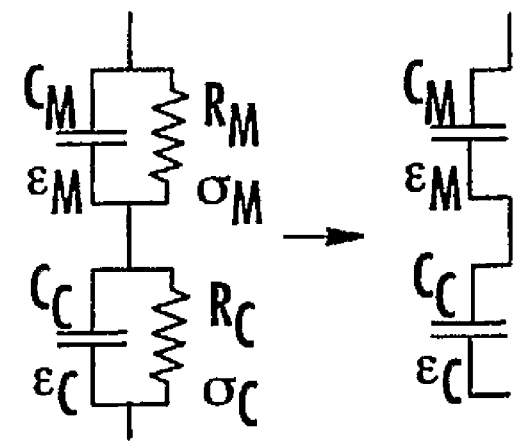
FIG. 4 is a schematic illustration showing the equivalent circuit of a biological cell (single shell model) for extremely short pulses, generally less than 1 ns.

The assumptions used in most models for membrane charging and electroporation as well as intracellular electromanipulation, are that the membranes are perfect insulators, and that the permittivity of the liquids in and outside the cell can always be neglected. This assumption reduces the general equivalent circuit for a single shell cell to the one shown in FIG. 3. This equivalent circuit is well suited to describe poration processes at cell membranes and shows the times that are short relative to the dielectric relaxation time (the product of resistivity and permittivity) of the membrane(s), and to times that are long relative to the dielectric relaxation time of the cytoplasm and nucleoplasm. Based on data for the electrical properties of mammalian cells [11], this equivalent circuit (FIG. 5) is applicable to a pulse duration range from approximately one nanosecond to microseconds, depending on cell type.

Table 1. Electrical parameters of biological cells as measured using time domain dielectric spectroscopy

TABLE 1

Dielectric parameters of cell structural parts for all cell populations studied.

| Cells | $\epsilon_m \pm 12\%$ | $C_m$ µF/Cm² ± 12% | $10^{-6} \sigma_m$ S/m ± 25% | $\epsilon_{ne} \pm 30\%$ | $C_{ne}$ µF/cm² ± 30% | $10^{-3} \sigma_{ne}$ S/m ± 30% | $\sigma_{cp}$ S/m ± 18% | $\sigma_{np}$ S/m ± 22% |
|---|---|---|---|---|---|---|---|---|
| B-cells | | | | | | | | |
| B-normal | 12.8 | 1.6 | 56 | 106 | 2.3 | 11.1 | 1.31 | 2.04 |
| Magala | 11.4 | 1.4 | 8.8 | 72.5 | 1.6 | 3.7 | 0.55 | 1.08 |
| Farage | 9.8 | 1.2 | 9.1 | 60.3 | 1.3 | 4.4 | 0.48 | 1.07 |
| Raji | 8.8 | 1.1 | 8.2 | 79.9 | 1.8 | 4.0 | 0.58 | 1.02 |
| Bjab | 8.0 | 1.0 | 11.0 | 108 | 2.4 | 2.1 | 0.88 | 1.39 |
| Daudi | 7.2 | 0.9 | 9.5 | 66.1 | 1.5 | 2.7 | 0.85 | 1.44 |
| T-cells | | | | | | | | |
| T-normal | 11.1 | 1.4 | 27.4 | 85.6 | 1.9 | 8.8 | 0.65 | 1.26 |
| Peer | 9.5 | 1.2 | 12.9 | 61.6 | 1.4 | 2.1 | 0.81 | 1.42 |
| HDMAR | 7.4 | 0.9 | 14.5 | 101 | 2.2 | 3.0 | 0.88 | 1.58 |

The fit was made by fixing the following parameters: $\epsilon_{cp} = 60$, $\epsilon_{np} = 120$, d = 7 nm, $d_n$ = 40 nm, and Rn = R · $(0.6)^{1/3}$.

$\epsilon_{cm}$: permittivity of plasma membrane; $C_m$: capacitance of plasma membrane; $\sigma_m$: conductivity of plasma membrane; $\epsilon_{ne}$: permittivity of nuclear envelope; $C_{ne}$: Capacitance of nuclear envelope; $\sigma_{ne}$: conductivity of nuclear envelope; $\sigma_{cp}$: conductivity of cytoplasm; $\sigma_{np}$: conductivy of nucleoplasm; $\epsilon_{cp}$: permittivity of cytoplasm; $\epsilon_{ne}$: permittivity of nucleoplasm; d: thickness of plasma membrane; $d_n$: thickness of nuclear membrane; $R_n$/R: ratio of nuclear to cell diameter.

For very short pulses, the dielectric properties, rather than the resistive characteristics of the media, determine the electric field distribution. The equivalent circuit for a single shell cell is then determined by the dielectric properties only. The condition that the resistive term in the cytoplasm impedance can be neglected compared to the capacitive term, requires that the pulse duration is short compared to the dielectric relaxation time of the cytoplasm ($\epsilon_{cp}/\sigma_{cp}$). Based on the data listed in table 1, this is only true if the pulse duration is on the order of, or less than, one nanosecond. The electric fields in the various parts of the cell are then defined by the continuity of the electric flux density. For a membrane with a relative dielectric constant of 8, the electric field in the membrane is ten times higher than the electric field in the adjacent cytoplasm, which has a dielectric constant of 80. The electric field then acts directly on molecules, rather than causing charging of the membrane, and if sufficiently strong, can cause direct and instant conformational changes, such as voltage gating.

This range of operation, which is defined by the condition that the pulse duration is shorter than the dielectric relaxation time constant of the cytoplasm, nucleoplasm, and medium surrounding the cells, opens a new temporal domain for cell responses to pulsed electric fields. First modeling results by R. Joshi, using molecular dynamics simulation [12], have shown that such conformational changes can be expected when extremely short pulses are applied.

Pulsed Power System for Subnanosecond Bioelectric Studies: In order to explore the new regime in bioelectrics, the characteristic parameters of the electrical pulses need to be on the order of or less than the relaxation time of the cytoplasm, nucleoplasm and the supernatant. This is a value of less than one nanosecond. A pulsed power system, which is able to provide subnanosecond pulses to a biological load, has been designed and built. The advantage of this sparkgap-switched pulsed power device is the high voltage, low impedance, and relatively low cost. The disadvantage is the restricted repetition rate. Whereas semiconductor opening switch-based pulsed power generators can operate at rep-rates of up to 50 kHz in a burst mode, sparkgap switch-based systems are generally restricted to approximately 100 Hz.

The block diagram of the experimental system is shown in FIG. 5, including the cross-section of the exposure system.

The system is able to generate 0.8 ns voltage pulses with an amplitude of 350 kV into a 50Ω load. Voltages measured at the high impedance load reach values of 700 kV. With a gap distance of 4.25 mm, this corresponds to electric fields of 1.5 MV/cm. A voltage and current pulse shape is shown in FIG. 6. In spite of this extremely large field, no electrical breakdown was observed. This is in line with results obtained with 200 and 400 ns pulses, where the breakdown field for water reached these values in a pin-plate electrode configuration. With pulse durations reduced by two orders of magnitude compared to those used in the water breakdown experiments, even multi-MV/cm fields in the subnanosecond range don't lead to breakdown.

The Effect of Subnanosecond Pulses on Biological Cells: Experimental Results: In order to determine the lethal subnanosecond pulse effects on biological cells, we have used B16 Melanoma cells as target cells in a physiological medium. Trypan Blue was added to the suspension. Trypan Blue is a vital dye which binds to DNA after entering the cell and autofluoresces in the blue range of the spectrum. Since Trypan Blue enters the cell only if the membrane has disintegrated, it is generally used to indicate cell death. The cells were counted under a microscope after exposure, and the ratio of live cells to dead cells (indicated by Trypan Blue uptake) was recorded.

Figure 7:
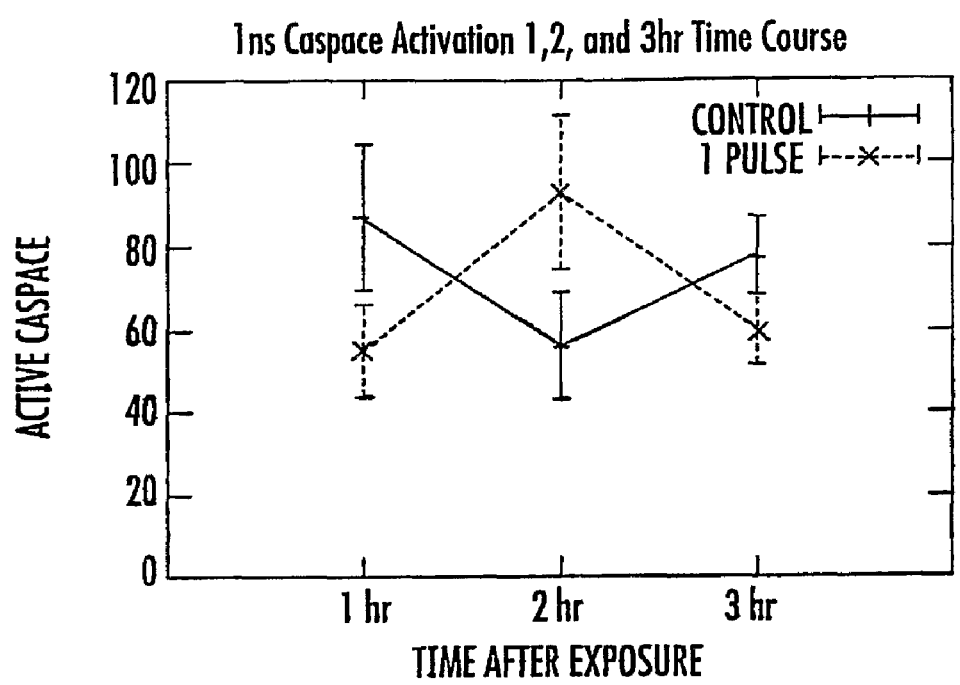
FIG. 7 is a graph showing caspase activation after a single pulse of 750 kV/cm and 0.8 ns duration was applied to a suspension containing B16 cells.

Experiments where B16 cells in suspension were exposed to single pulses of 0.7 MV/cm amplitude showed only a small effect on the viability of the cells. However measurements of caspase activation, an indicator for apoptosis, showed a considerable increase two hours after the cells were exposed to the 0.8 ns pulse (FIG. 7). It can therefore be expected that the ultrashort pulses, when applied multiple times, will cause cells in suspension, but also in tissue, to die through apoptosis.

However, when the cell viability was measured hours after exposure, a strong decrease in viability was observed (FIG. 8). Whereas the viability of the control cells stayed almost constant at 95%, the viability of the pulsed B16 cells after only one pulse exposure decreased over a time of 8 hours to values of 50%. This corresponds to an average dying rate of 5%/hour. The value leveled off after 24 hours (to be shown). This delayed change in viability indicates that programmed cell death, apoptosis, is occurring (reviewed in [16]. The majority of the cells, after being hit by this tremendous electric field pulse, is apparently so damaged that after initial repair attempts, programmed cell death sets in. Such death is known to occur on a time scale of hours after a physical or chemical insult, consistent with our results.

From Intrusive Delivery Systems to Antennas: The observed apoptotic effects of a single pulse in the subnanosecond time range will open the possibility of using such pulses for therapies where apoptosis induction is important: in all types of removal of unwanted cells and tissue, particularly tumors. Studies of such effects are now being performed using electrodes as pulse delivery systems to the cell suspension or tissue [10]. For therapeutic applications, however, the use of electrodes, such as needles or plates, restricts the pulsed electric field method to treatment of tissue close to the body surface. The use of antennas, on the other hand, would allow one to apply such electric fields to tissues (tumors) that are not easily accessible with needles. Also, the focusing of electrical energy on the target would reduce the damage to the skin and normal tissue layers surrounding the target.

In this respect, the use of subnanosecond pulses does not only allow us to extend the pulsed field interactions with biological cells into a new type of time domain, as described infra, but makes it possible to use ultrawideband antennas to deliver these pulses to targets within the body. The ultrashort pulse duration, which defines the possible spatial resolution for such pulses, can be brought into a range that allows the targeting of specific parts of the body. For a 0.8 ns wide pulse, the cut-off frequency is approximately 0.75 GHz. Therefore, the wavelength corresponding to the cut-off frequency in tissue with a dielectric constant of 80 is approximately 5 cm, a value which determines the spatial resolution for such a pulse in tissue. It indicates the importance of reducing the pulse duration to the absolute minimum.

Figure 9B:
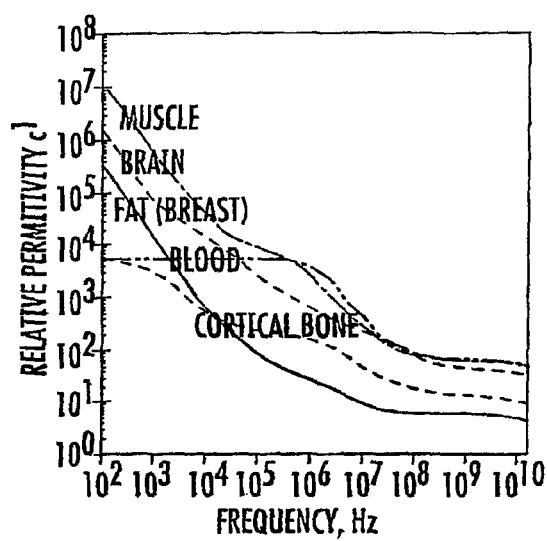
Figure 10:
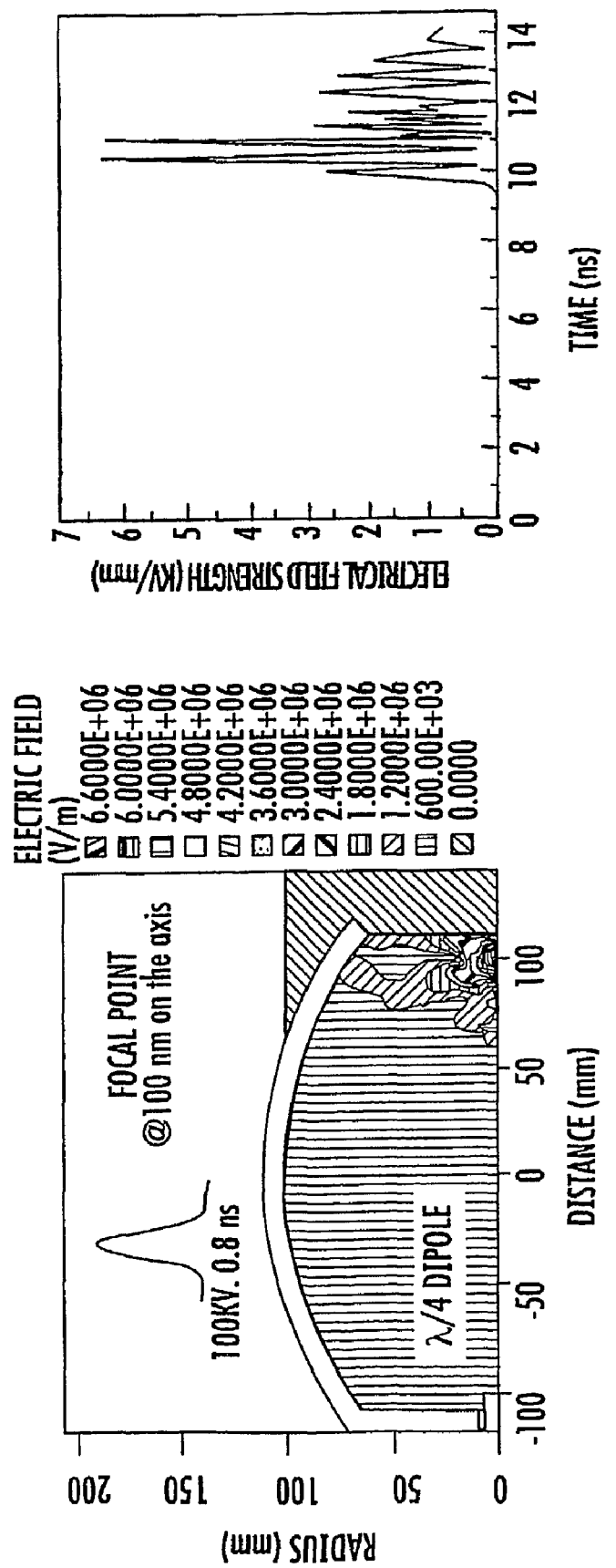

Generally, wideband antenna design is geared towards the generation of large electromagnetic fields in the far-field. An example for such an antenna, which generated an electric field of 600 V/cm at a distance of 100 m from the antenna. For bioelectric applications, however, it is important to generate even larger electric fields in smaller volumes. A design that allows us to produce very high electric fields in restricted volumes is based on a geometrical concept: The power radiated from a point source located in one focal point of an ellipsoidal reflector is focused in the second focal point. This concept, and its application to focusing the electromagnetic energy in a small volume inside a tissue, is illustrated in FIG. 8. The source is located in the focal point of the ellipsoidal reflector on the left side. The electromagnetic waves reflected from the reflector are focused in the second focal point (right side) that is located in tissue. In order to reduce reflections at the tissue surface, the complex permittivity of the medium filling the space outside the tissue will be of approximately the same value as that of the tissue. Examples for tissue values are given in FIGS. 9A and 9B. Permittivities in the 1 ns range (fundamental frequency approximately 100 MHz to 1 GHz) are in between 10 and 100. Conductivities vary between 0.02 to 1 S/m. Such values can be obtained with mixtures of water and low permittivity liquids. However, due to the relatively large conductivity of such liquids, the attenuation of the wave traveling from the source to the target, can limit the obtainable electric fields at the target considerably. A compromise would be the use of low conductivity (distilled and deionized) water or other polar liquids, or even nonpolar liquids such as oil.

Figure 12:
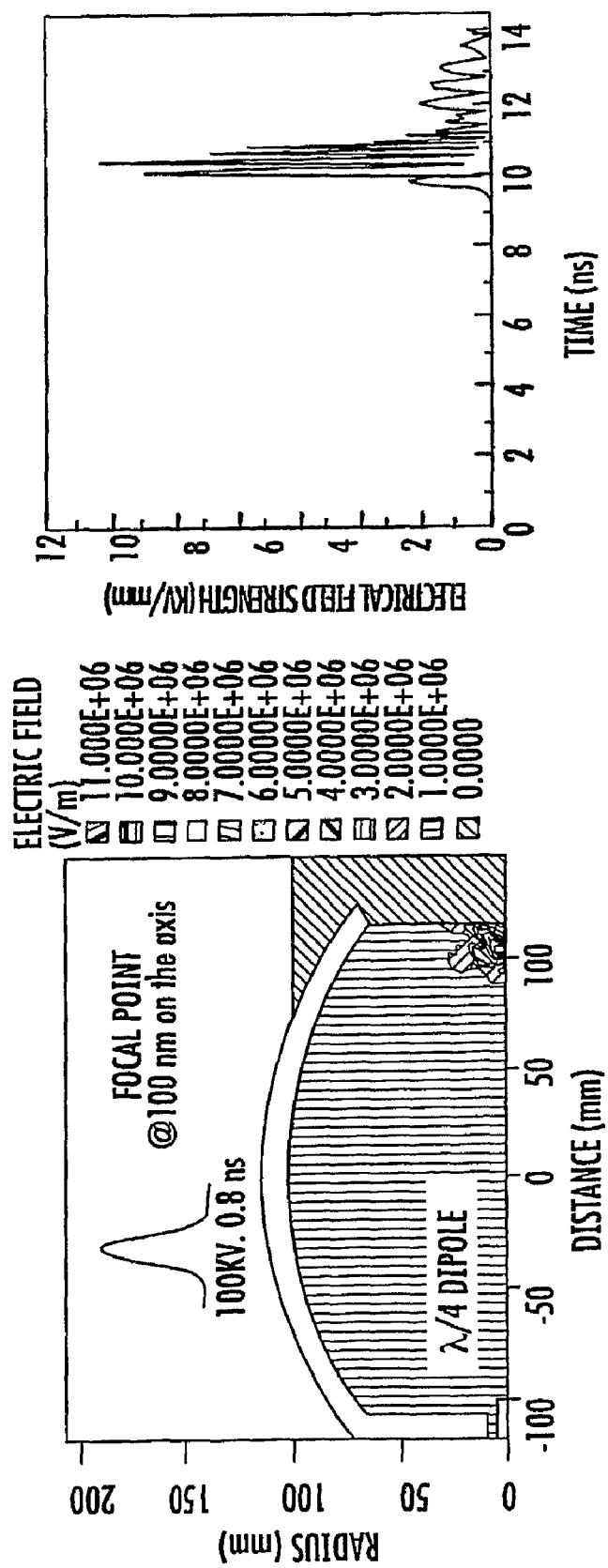

Time-domain computations, based on Maxwell solvers with "perfectly absorbing boundary conditions" for the overall simulation region, have been used to model the development of the electric field in the focal point of an ellipsoidal antenna with stimulation by a quarter wave dipole. An existing numerical software package of simulation tools (MAGIC) has been used. The geometry of the antenna and source, the spatial distribution of the electric field intensity at the second focal point at the time of maximum field, as well as the temporal development of the amplitude at the target are depicted in FIGS. 10, 11, 12, and 13. The target, a part of a human body would be placed right where the highest electric field concentration is—in the second focal point. The calculations show clearly the influence of the antenna, as well as the pulse duration: Optimum results are obtained with almost closed antennas (FIGS. 10 and 12) and short pulses (FIGS. 12 and 13). The applied voltage in all cases was 100 kV.

Example 2

Ultrawideband Antenna for Near-Field Operation in Tissue

Intracellular electromanipulation requires electric fields on the order of 10 kV/cm to 300 kV/cm when 10 ns pulses are applied for single shot operation. The range in electric field strength reflects the range in effects: for low electric fields, we have observed nonlethal effects based on calcium release, for high electric fields, apoptosis has been achieved. This is the case for single-shot operation. For multiple-shot operation at 10 ns, the electric field could be reduced to values below 100 kV/cm, with apoptosis still being observed. Besides the electric field, the pulse duration plays an important role. Based on the results of experiments, any intracellular effect seems to scale with the product of pulse duration and electric field intensity. This means that any decrease in pulse duration needs to be compensated by an increase in electric field. For a 1 ns pulse, assuming multiple shot conditions, apoptosis would require electric fields close to 1 MV/cm. For a nonlethal effect such as calcium release (which in turn could have a number of secondary effects, such as platelet activation, neural stimulation, etc.), the required electric field would be lower, but probably still in the range of hundreds of kV/cm.

Antenna Parameters: In order to generate electric fields of this amplitude by antennas of reasonable size and power, cells, tissues or patients were exposed to the near field of the antenna. The near field is defined as the region bounded by a sphere with a radius of less than the wavelength divided by $2\pi$.

In order to "focus" these fields in a limited spatial area, the principle of superposition is used (for far-field applications, this principle is used in phased array antenna systems). Focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

The use of wideband antennas the construction of a pulse generator comprises the following features: Pulse duration: <1 ns; Voltage: <1 MV; Impedance: on the order of k$\Omega$.

A 200 kV, 1 ns pulser is already available. The same Marx-bank concept is used to build a higher voltage system. In order to use the superposition principle, a dual coax antenna can be used, where the two waves can be phase-shifted to achieve highest fields where needed. Modeling results using an existing code, "MAGIC®", indicate that this approach is successful. Measurements of the electric field distribution in water, resembling the electrical properties of tissue, will be performed using the Kerr effect. A Mach-Zehnder interferometer is available and has been tested in evaluating water discharges.

The invention comprises: a high voltage (up to MV) ns pulse generator; a dual coax antenna; modeling the electric field distribution in tissue, dependent on a phase shift between the two coaxial waves, and, measuring the electric field distribution in water using the Kerr effect.

Antenna Parameters: 1. Near Field Antenna (target very close to electromagnetic wave source). (a) In order to generate electric fields of this amplitude by antennas of reasonable size and power, cells, tissues were placed in the near field of the antenna. The near field is defined as the region bounded by a sphere with a radius of less than the wavelength divided by $2\pi$. (b) The spatial resolution for such near field "antennas" is determined by the electrode dimensions. In a coaxial cable which is used as catheter this would be the diameter of the center conductor and the distance to the surrounding, coaxial conductor. In a dual-coaxial "antenna, where the center conductor is surrounded by two coaxial cylinders where the inner coax-cable delivers one pulse, and the outer coax cable (determined by the two outer coaxial conductors) the second, phase shifted pulse the principle of superposition is used (for far-field applications, this principle is used in phased array antenna systems) to "focus" these fields in a limited spatial area. (c) In the dual-coax system focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

Antenna Parameters 2. Focusing Antenna (distance of target to source determined by the focusing device which can be either a lens or a reflector). a) In order to generate electric fields of this amplitude by antennas of reasonable size and power, cells, tissues were placed in the focal point volume of the antenna. The focal point volume is defined as the region bounded by a sphere with a radius on the order of the wavelength, centered at the focal point. (b) In order to focus these fields in a limited spatial area, focusing reflectors or lenses are used. (c) Focusing with a spatial resolution of cm requires the fundamental wavelength of the wide-band pulse generator to be on the same order. For air, this would require a bipolar pulse with a total duration of 30 ps. For water, with a dielectric constant of 81, this is increased to 270 ps or 0.27 ns. Pulses with 1 ns duration would provide a spatial resolution of 3 cm.

Example 3

Nanosecond Pulsed Electric Fields Cause Melanomas to Self-Destruct

Electric fields have been employed in several different types of cancer therapy. Some of these involve radiofrequency or microwave devices that heat the tumor to greater than 43° C. to kill the cells via hyperthermia. Others use pulsed electric fields to permeabilize the tumor cells to allow the introduction of toxic drugs or DNA. We have discovered that ultrashort electrical pulses can be used as a purely electrical cancer therapy that kills tumors without hyperthermia or drugs. Previous work from this laboratory found that fibrosarcoma tumors treated in vivo with ten 300 ns pulses exhibited a reduced growth rate compared to control tumors in the same animal (S. J. Beebe, et al., IEEE *Trans. Plasma Sci.* 30 (2002) 286-292). Here, we report that when melanoma tumors are treated with four hundred of these pulses, tumors shrink by 90% within two weeks and a subsequent treatment can result in complete remission.

The main characteristics of these nanosecond pulsed electric fields (nsPEF) are their low energy that leads to very little heat production and their ability to penetrate into the cell to permeabilize intracellular organelles (K. H. Schoenbach, et al., *Bioelectromagnetics* 22 (2001) 440-448; E. S. Buescher, et al., IEEE *Trans. Dielect. El. In.* 10 (2003) 788-794) and release calcium from the endoplasmic reticulum (J. A. White, et al., *J. Biol. Chem* 279 (2004) 22964-22972). They provide a new approach for physically targeting intracellular organelles with many applications, including the initiation of apoptosis in cultured cells and tumors, enhancement of gene transfection efficiency, and inhibiting tumor growth. During the past year, we have treated over 300 murine melanomas in 120 mice with 40 kV/cm electric field pulses 300 ns in duration with dramatic results. Every tumor exposed to 400 such pulses exhibits rapid pyknosis and reduced blood flow and shrinks by an average of 90% within two weeks. A second treatment of 300 pulses can completely eliminate the melanoma. This very short total field exposure time of only 210 μs stimulates melanomas to self-destruct without drugs or significant side effects. How do these nanosecond pulsed electric fields penetrate into the cell and have such dramatic effects?

The efficacy of this nsPEF treatment depends on two separate electric field parameters: pulse duration and amplitude. The effect of pulse duration can be understood by considering the process of membrane charging when the cell is placed in an electric field. Ions in the cell interior will respond to the electric field by moving in the field direction and charging the highly resistive membrane until they experience no further force. By definition this will only occur when their redistribution establishes an equal and opposite field so that the net electric field in the cell interior is zero. However, this redistribution takes a certain amount of time that is characterized by the charging time constant of the plasma membrane, typically in the 0.1-1 μs range. If the nsPEF is shorter than this charging time, the interior charges will not have sufficient time to redistribute to counteract the imposed field and it will penetrate into the cell and charge every organelle membrane for a duration which is dependent on both the charging time constant of the cell's plasma membrane as well as that of the organelle membrane.

The second critical nsPEF parameter is the amplitude of the pulse. Both the force exerted on charges and the electroporation of lipid membranes depend on the strength of the electric field. When the electric field across a cellular membrane exceeds about 1 V (2 kV/cm for a cell 10 μm in diameter), water-filled pores form in the membrane's lipid bilayer and the size and lifetime of these pores are dependent on the strength and duration of the electric field pulse. For amplitudes exceeding 2 kV/cm and pulse durations in the millisecond range, large pores form resulting in electroporation of the membrane that has been used to introduce normally impermeant anticancer drugs into targeted tissues (J. Teissie, et al, *Biochim. Biophys. Acta* 1724 (2005) 270-280). For these long pulses, the pulse amplitude is limited to about 2 kV/cm to avoid thermal effects. Since heating is proportional to pulse duration and the square of the field strength, the much shorter pulses in the nanosecond range can have a higher field strength while delivering the same low level of thermal energy to the tissue. Here, we use a 20-fold higher field strength of 40 kV/cm and this generates structural changes in the plasma membrane that result in a smaller electrical barrier as well as higher voltage gradients across cellular organelles for the duration of the pulse. A typical tumor cell nucleus measuring 10 μm in diameter will experience a voltage gradient of roughly 40 V across its diameter during each pulse. This electric field is large enough to cause electrodeformation (R. P. Joshi, et al., *Phys. Rev. E Stat. Nonlin. Soft. Matter Phys.* 65 (2002) 021913).

Cell tissue culture. Murine melanoma B16-F10 cells were obtained from ATCC (Manassas, Va.) and were stored frozen in liquid nitrogen until needed. They were thawed in a 37° C. water bath and then transferred to a culture flask containing DMEM (Dulbecco's modified Eagle's medium) supplemented with 10% fetal bovine serum (FBS, Atlanta Biologicals), 4 mM L-Glutamine (Cellgro), and 2% Penicillin-Streptomycin solution (Cellgro). The cells were grown in a 5% $CO_2$/95% air/100% humidified incubator at 37° C.

Melanoma induction. Two to four tumors were induced in 120 female SKH-1 mice (immunocompetent, hairless, albino strain, Charles River, Wilmington, Mass.) by injecting 2-10 μl containing $10^6$ B16-F10 murine melanoma cells just under the skin in the loose areolar tissue. A melanoma tumor can be seen at the injection site within a few days. Within 5 days the tumor is typically 3 mm wide and has exhibited angiogenesis. Untreated tumors typically grow to 10 min wide or more within a few weeks. For all animal studies the mice were kept under inhalation anesthesia using 1.6% isoflurane in oxygen. Tumors in animals #4 to #63 were treated with a 5-needle electrode array and #64 to #120 were treated with parallel plate electrodes. In a typical experiment, two tumors were used as controls and two others on the same mouse were treated with nsPEF.

In vivo imaging. Melanomas were imaged daily by both transillumination and surface photography at 1.2·× magnification and ultrasound-images were also taken beginning with mouse 50. Visualsonics Vevo 770 (Visualsonics Inc., Toronto, Canada) was used to image tumors in vivo. We used their model 708 scan head at 55 MHz with a stepper motor scanner providing a spatial resolution of 30 μm. The power Doppler mode provided blood flow images for each tumor.

Histology. Phosphate-buffered formalin (10%) was injected into the loose areolar layer under the skin at the tumor site immediately after euthanizing the mouse and 15 min prior to tumor dissection. The tumor was placed in formalin fixative (minimum 20·× tumor volume) for 24-48 h at room temperature. The tumor and surrounding skin were trimmed and both external and internal surfaces were photographed. The fixed tumor was dehydrated through a standard 30%, 50%, 70%, 80%, 90%, 95%, and 100% X3 ethanol series, cleared in 100% X2 xylene, infiltrated at 60° C. in molten paraffin baths X2 (all for 1 h each), and then embedded in a paraffin block. Seven micrometer thick sections were cut and stained with hematoxylin and eosin.

Figure 16A:
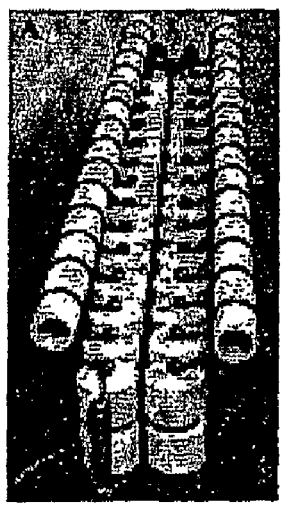
FIGS. 16A-16B are diagrams showing the pulse generator used in these experiments.
Figure 16B:
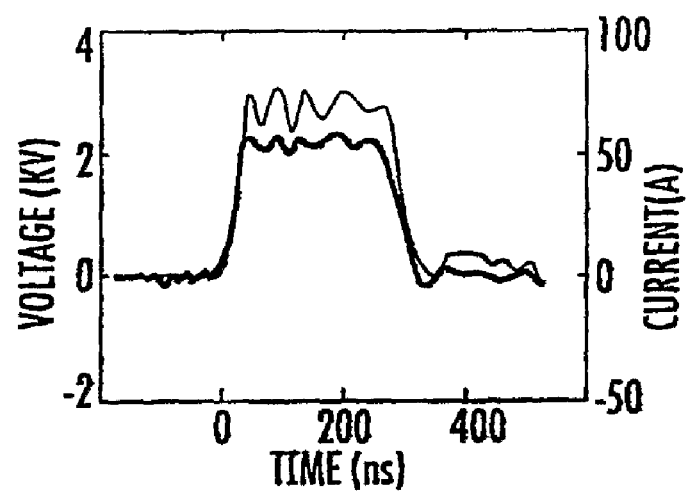

Pulse generator. We used a pulse-forming network with an impedance of 75Ω. It consists of 30 pairs of high voltage capacitors and 30 inductors arranged in a Blumlein configuration, and generates a 300 ns long high voltage pulse (J. F. Kolb, S. Kono, K. H. Schoenbach, Nanosecond pulsed electric field generators for the study of subcellular effects, Bioelectromagnetics (2006), in press) (FIGS. 16A and 16B). The pulse was originally triggered by means of a spark gap that was later replaced by a mercury displacement relay controlled by a microcontroller. The voltage across the object was monitored using a high voltage probe (P6015A, Tektronix, Beaverton, Calif.), and the current was measured by means of a Pearson coil (model 2877, Pearson Electronics Inc., Palo Alto, Calif.). Current and voltage were recorded simultaneously using a digitizing oscilloscope (TDS3052, Tektronix, Beaverton, Oreg.).

Figure 17A:
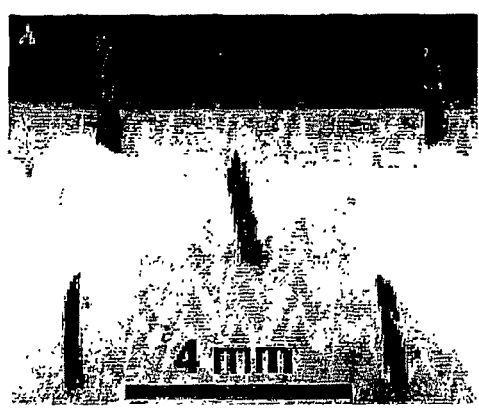
FIGS. 17A and 17B show the needle array electrode and electric field pattern.
Figure 21A:
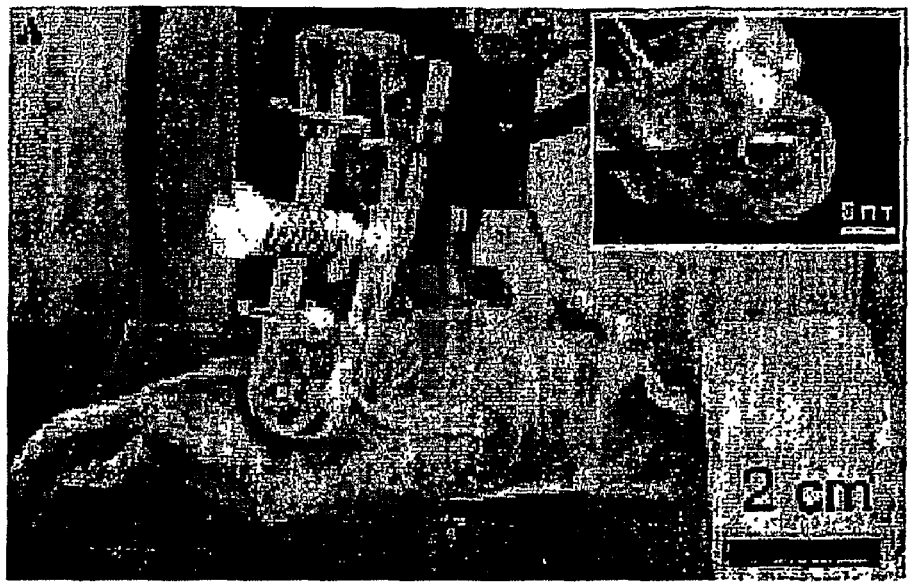
FIG. 21A is a scan of a photograph showing SKH-1 hairless mouse being treated with parallel plate electrode under isoflurane inhalation anesthesia. (Inset) Close-up of one of the plates of parallel plate electrode showing it recessed by 0.5 mm to allow a space for a conductive agar gel to be placed on it.

Electrodes for electric field application. We used two types of electrodes, a 5-needle array and parallel plates. The needle array (FIGS. 17A and 17B) was made using 30 gauge hypodermic needles (300 lm diameter) extending 2 mm from a Teflon base. The center needle was the anode and the four surrounding needles spaced 4 mm from the center electrode were connected together forming the cathode. The skin was coated with vegetable oil prior to needle insertion to increase the breakdown field strength along the skin and reduce the likelihood of flashover between needles during the pulsed field application. The parallel plate electrodes (FIG. 21A)

were made from stainless steel with diameters of 3-5 mm, depending on the size of the tumor being treated. We coated these electrodes with a 0.5 mm thick layer of conductive agar (1 M NaCl in 2% agar) to separate the skin from the electrode. For treatment, each tumor was positioned between two plates with a separation of 0.5-1 mm, while 100 pulses 300 ns ill duration and 4-8 kV in amplitude with a rise time of about 30 ns were applied at a frequency of 0.5 Hz.

Determination of caspase activation in vitro. Caspase activity was determined in vitro from melanoma tumor extracts after exposure to nsPEF. Melanomas were dissected out of the mouse and frozen in liquid nitrogen. Extracts were prepared from thawed tissue homogenates and assayed for caspase activity using the fluorogenic substrate Ac-DEVD-AFC (Alexis Biochemicals, San Diego, Calif.) as previously described (L. K. Parvathenani, et al., *J. Biol. Chem.* 273 (1998) 6736-6743). This peptide sequence is based on the PARP cleavage site, $Asp^{216}$, for caspases 1, 3, 4, and 7, that exhibits enhanced fluorescence upon cleavage. Briefly, extracts were incubated with 50 1 M DEVD-AFC (Asp-Glu-Val-Asp-AFC) and fluorescence (excitation 400 nm and emission 505 nm) was determined. Caspase units were defined as picomoles of substrate cleaved per minute per milligram extract protein.

Figure 17B:
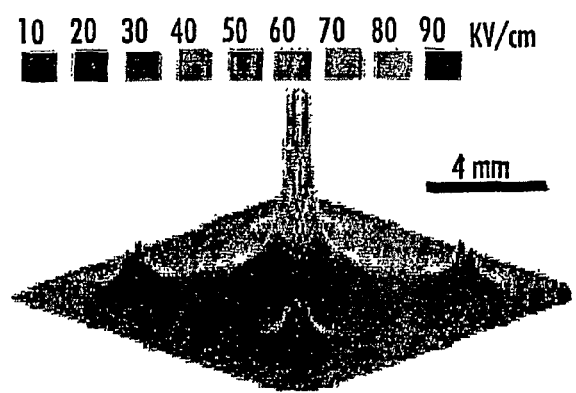
Figure 18:
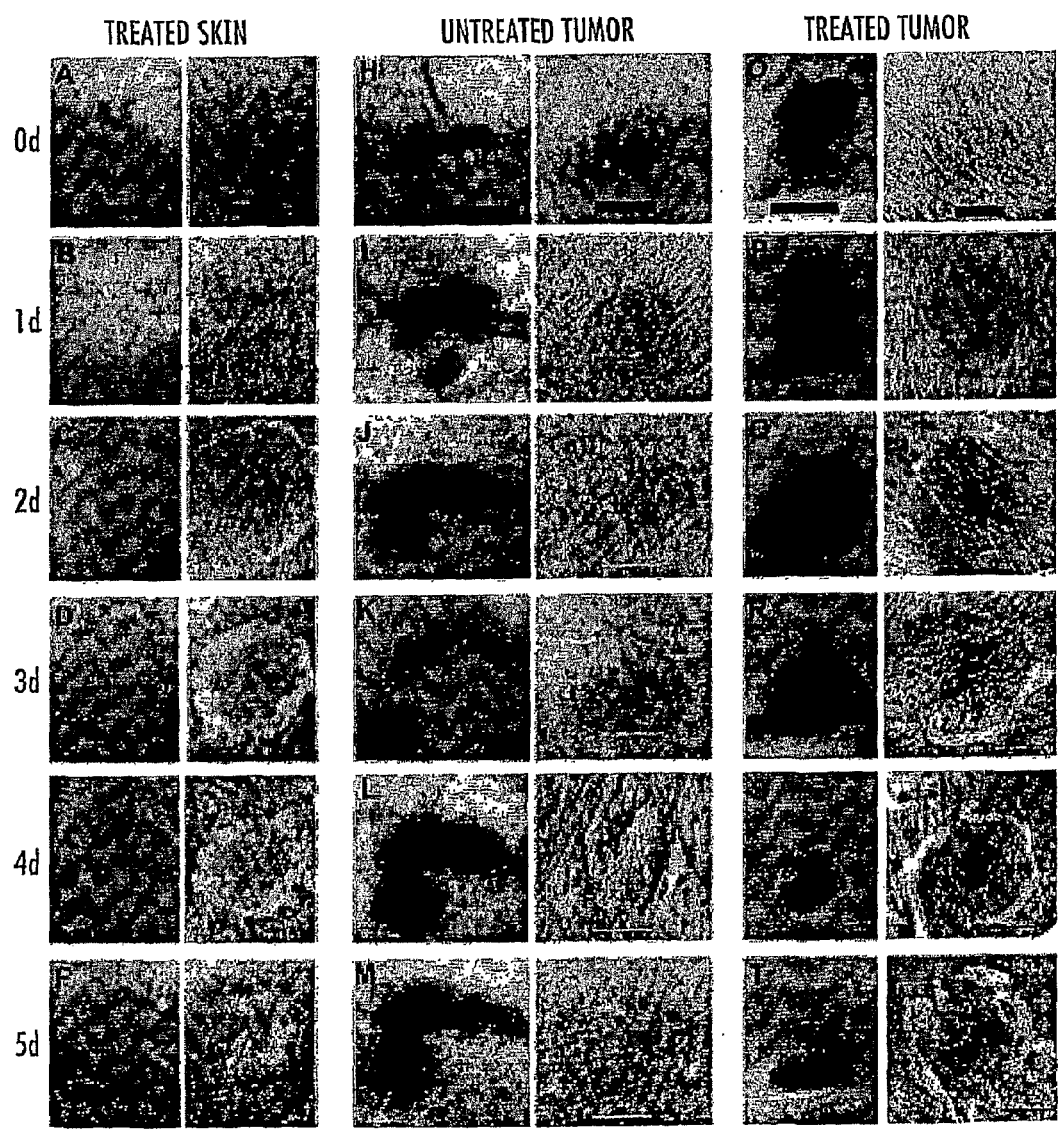

Results and discussion: The electric field was applied using two different electrode configurations. The first was a 5-needle electrode array (FIG. 17A) in which the needles penetrated about 2 mm into the mouse skin. In 59 mice, the central needle was placed in the center of the melanoma to be treated and the outer four needles were outside of the boundary edges of the melanoma. This electrode array exhibits a sharply non-uniform field with field lines parallel to the surface of the skin and strongest near the center electrode (FIG. 17B). When the needle array is inserted into a melanoma for a couple of minutes and removed, the melanoma continues to grow normally (FIGS. 18H-18M). However, if 100 pulses (8 kV, 300 ns, 0.5 Hz) are administered to the needle array prior to removal, the melanoma begins to shrink within 2 days (FIGS. 18O-18T). Blood flow to the tumor is disrupted after pulsing as red blood cells leak out of capillaries surrounding the tumor (FIG. 18P). Local blood flow usually does not recover for about two weeks. Two days after pulsing, the stratum corneum shows signs of necrosis and hemorrhage with accompanying superficial erosion of the epidermis and the tumor becomes darker (FIG. 18Q). This suggests that in addition to the tumor cells, the epidermal cells of the skin between the electrodes that differentiate into the stratum corneum are damaged by the 300 ns pulsed electric field (nsPEF). We confirmed this by treating skin regions where there were no melanomas and observing similar superficial erosion over the same time period (FIGS. 18A-18F). Insulating the upper shaft of the needles that come into contact with the epidermis may reduce this damage.

Figure 19A:
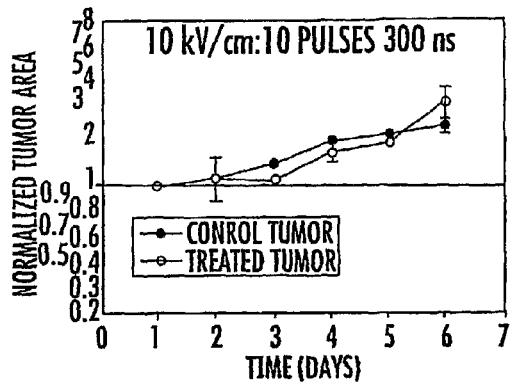
FIGS. 19A-19E are graphs showing a summary of the size changes in a total of 23 melanomas after the indicated treatments using the 5-needle array. For each day the tumor area was measured from the transillumination image and divided by that measured on day zero to give the normalized area. The average response of two to three tumors from different animals is plotted on a logarithmic scale and the error bars represent the SEM. Pulses were applied at a frequency of 0.5 Hz.
Figure 19B:
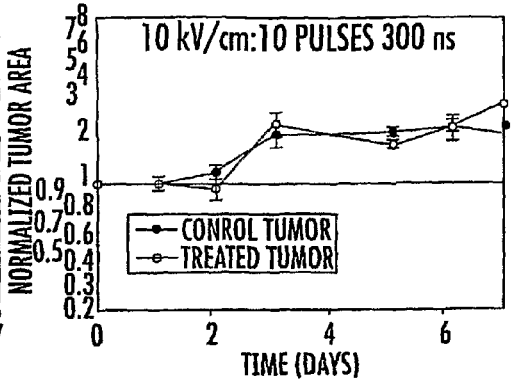
Figure 19C:
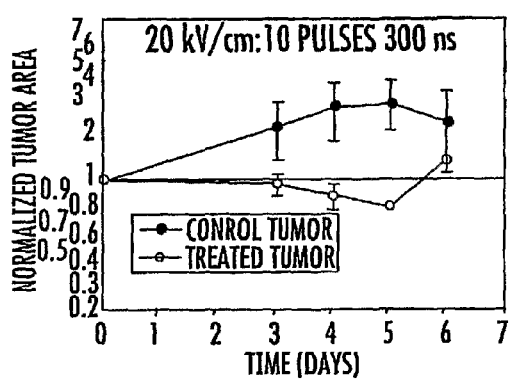
Figure 19D:
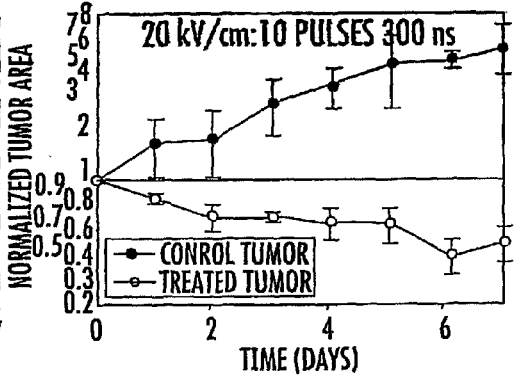
Figure 19E:
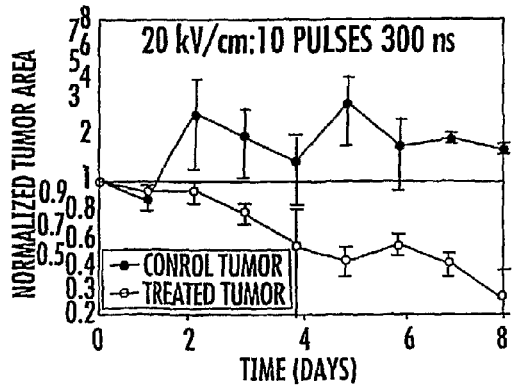

This tumor response is dependent on both field strength and pulse number. If the field strength is cut in half by using a 4 kV pulse (average field of 10 kV/cm), there is no significant difference between the growth rates of treated and control tumors (FIG. 19A). This holds true for the application of both 10 and 100 pulses (FIG. 19B). The pulse number dependence is more evident for the 8 kV pulses (20 kV/cm field) where the response is stronger for 100 pulses than it is for 10 (FIGS. 19C and 19D) and even stronger when two treatments of 100 pulses are given (FIG. 19E). Under this latter condition, the tumors shrink by about 75% within 8 days.

Figure 21B:
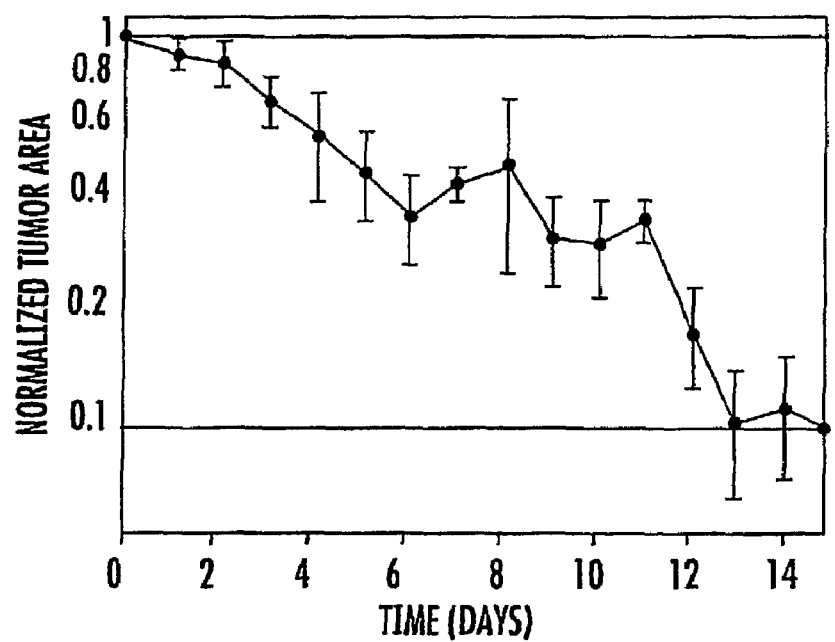
FIG. 21B is a graph showing the mean change in normalized area of the transillumination image of six tumors from three mice treated with parallel plate electrodes using the same 4×100 pulse applications (3×100 on day 0 and 1×100 on day 4). 40-80 kV/cm, 300 ns pulses at 0.5 Hz. Error bars indicate the SEM.

The second electrode configuration used involved placing the tumor between two parallel plates (FIG. 21A). The electric field between two parallel plates is uniform except at the edges, so that all cells between the plates will be exposed to the same field strength. These electrodes were used when treating 48 mice by lifting a fold of skin containing the melanoma away from the mouse and placing it between the electrodes in such a way that the entire tumor was positioned between the plates. Thus, the field was oriented perpendicular to the skin surface rather than parallel to it as with the needle electrodes. The distance between the plates was typically 0.5-1 mm, depending on tumor thickness. Based on our previous results with needle electrodes, we used a field strength of 40 kV/cm and the typical response to nanosecond pulses with this electrode configuration is illustrated in FIGS. 20A-20D. One difference between the two electrode types is the appearance of the skin beginning two days after treatment. A black scab appears on the stratum corneum in the pulsed region and it remains for about two weeks as the stratum corneum is regenerated (FIG. 20B). Histological examination of this scab indicates that it is composed of clotted red blood cells. Tumors typically shrank by 90% within two weeks following four 100-pulse treatments using plate electrodes (3 on day 0 and 1 on day 4) (FIG. 21B). However after about two weeks of regression, all tumors began to grow again and we sacrificed the mice at that time so that we could fix and section the tumors for histology.

Figure 22:
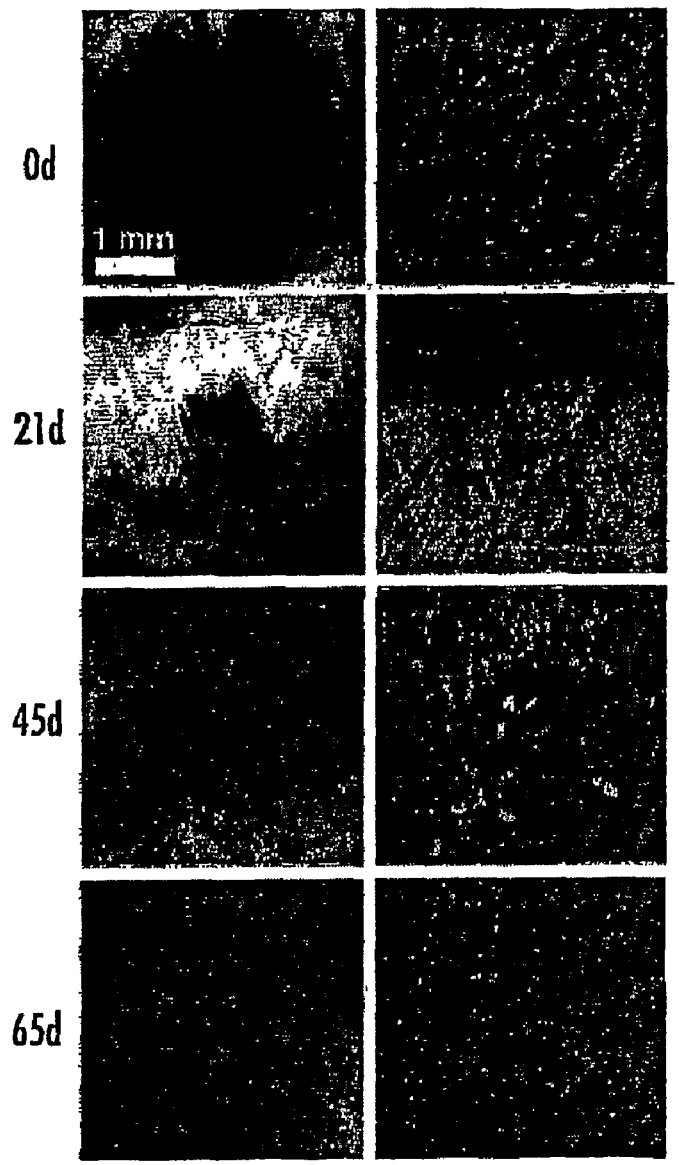
FIG. 22 is a scan of a photograph showing complete regression of melanoma evident by 65 days after the first treatment. One hundred pulses of 300 ns and 40 kV/cm were applied on days 0, 1, 2 and 21, 22, 23. Each pair of photographs were taken on the day indicated at the left; transillumination on left and surface view on right. The scale bar in upper left represents 1 mm and is the same for all images.
Figure 23A:
FIGS. 23A-23B show the measurement of the temperature within a melanoma during nsPEF application.
Figure 23B:
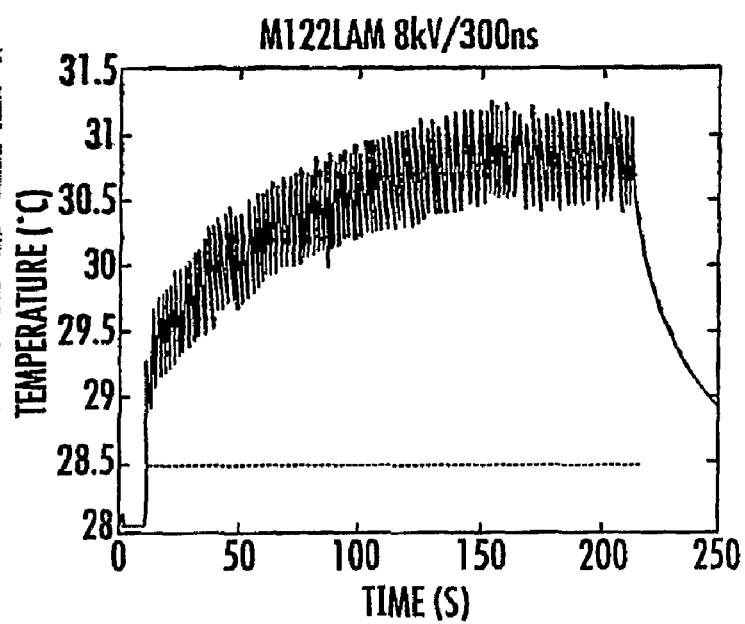

Multiple treatments result in complete tumor remission. We have begun to treat tumors with a second 3-day series of 100 pulses when they stop shrinking two to three weeks after the initial treatment. In three completed cases now, we have observed total remission of the tumor and one example is shown in FIG. 22. Within two months of the initial treatment, the melanoma was undetectable by transillumination, ultrasound or serial section histological investigation. We believe that further optimization of the nsPEF parameters should make it possible to routinely eliminate these skin tumors at a high rate of efficacy.

nsPEF Raises tumor temperature only 3° C. The energy delivered to the tissue between 5 mm plates is 0.2 J if the plate separation is 1 mm. Given the specific heat of water, this should only increase the tissue temperature by two to three degrees. We directly measured this temperature increase by inserting a very small thermocouple into the tumor and confirmed that the maximum temperature reached after 100 pulses was 33° C. (FIGS. 23A-23B). This is ten degrees lower than the minimum temperature required for hyperthermia effects so it is very unlikely that effects of nsPEF on tumor growth are due to hyperthermia.

Targets and potential mechanisms for nsPEF effects: We have identified two immediate changes in the tumor following the application of the electric field pulses that may be responsible for the tumor regression: (1) tumor cell nuclei rapidly become pyknotic and (2) blood stops flowing to the tumor. Untreated tumor cells exhibited lightly staining pleomorphic nuclei and abundant cytoplasm containing finely dispersed melanin granules (FIGS. 24A-24E). Treated tumors exhibited dense staining, shrunken nuclei, and dyshesion of individual cells with coarse intracellular melanin granules as well as aggregated extracellular melanin granules in the widened interstitial spaces. The tumor cell nuclei shrink by 54% within a few minutes after pulsing and by 68% within 3 h. No further nuclear shrinkage occurred during the subsequent two weeks as the tumor decreased in size by 90% (FIG. 24E). Some of the tumor nuclei elongate along the electric field axis but this is not always observed. The tumor cells themselves also shrink over this time period because the cell density is higher by one and three hours post-treatment. The nuclear pyknosis that follows pulse application occurs faster than any previously observed pyknotic response (S. M.

Albarenque, K. Doi, *Exp. Mol. Pathol.* 78 (2005) 144-149) and may result from either electrodeformation or the direct electric field interaction with cytoskeletal elements associated with the cell's nuclear lamina to generate the nuclear elongation and shrinking (P. K. Wong, et al, *J. Biomech.* 38 (2005) 529-535; Y. Gruenbaum, et al., *Nat. Rev. Mol. Cell. Biol.* 6 (2005) 21-31).

The second major change that is immediately obvious is a reduction in blood flow to the tumor. Both transillumination and power Doppler ultrasound reconstructions indicate that the blood flow has stopped within about 15 min after pulsing (FIGS. 25A-25D). Histology confirms that red blood cells are found scattered within and around the melanoma tumor. This implies that the local blood vessels become leaky and red blood cells escape into the surrounding tissues. Blood flow to the tumor does not normally recover for about two weeks. If blood flow returns, the tumor usually begins growing again. This lack of blood flow to the melanoma certainly contributes to its regression.

We also looked for changes in the classical apoptosis marker, caspase activity. We measured the activity of caspases using a fluorogenic substrate Ac-DEVD-AFC at 0, 3, 6, and 9 h after treatment with 100 pulses in three experiments. The only time at which caspase activity appeared to increase was at 3 h when there was a 2.6-fold increase in mean activity. However, this small change failed the normality t test and the Mann-Whitney Rank Sum test indicating that it was not a statistically significant difference (p=0.1). It is possible that an apoptosis program is initiated, but since apoptosis is an energy-requiring process, the interruption of the blood supply to the tumor may prevent completion of the apoptosis mechanism.

Our data support the hypothesis that nsPEF can produce DNA damage. The precise mechanism by which this damage is induced is not clear. Two possible mechanisms include activation of DNases in the apoptotic pathway or mechanically induced DNA breakage. A typical tumor cell nucleus measuring 10 lm in diameter will experience a voltage gradient of about 40 V across itself during each pulse. This electric field is large enough to cause rapid electromechanical deformation of the nucleus generating a mechanical shock to the DNA attached to the nuclear envelope that could damage the DNA. These nsPEFs stimulate murine melanomas to self-destruct by triggering rapid pyknosis and reducing blood flow without significant increases in caspase activity. A reduction in blood flow to tumors has also been observed following electrochemotherapy but does not occur until 24 h after treatment when the bleomycin entry had destroyed the endothelial cells. In contrast, nsPEF requires no drugs to achieve this dramatic reduction in tumor blood flow. This cellular response to a new nanosecond time domain of pulsed electric field application is both novel and deadly. This may have advantages over the surgical removal of skin lesions because incisions through the dermis often leave scarring on the healed skin. nsPEFs affect the tumor without disrupting the dermis so that scarring is less likely. nsPEFs should also be effective on other tumor types located deeper in the body if a catheter electrode is guided to the tumor. This highly localized and drug-free physical technique offers a promising new therapy for tumor treatment.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

All references cited herein, are incorporated herein by reference.

REFERENCES

[1] Schoenbach, K. H., Joshi, R. P., Kolb, J. F., Chen, N., Stacey, M., Blackmore, P. F., Buescher, E. S., and Beebe, S. J., (2004) "Ultrashort Electrical Pulses Open a New Gateway into Biological Cells, Proc. IEEE, 92, 1122.

[2] Schoenbach, K. H., Beebe, S. J., and Buescher, E. S. (2001). "Intracellular effect of ultrashort electrical pulses." Bioelectromagnetics 22, 440-448.

[3] Buescher, E. S. and Schoenbach, K. H. (2003). "Effects of submicrosecond, high intensity pulsed electric fields on living cells-intracellular electromanipulation." IEEE Transactions on Dielectrics and Electrical Insulation 10, 788-794.

[4] Vernier, P. T., Sun, Y. H., Marcu, L., Craft, C. M., and Gundersen, M. A. (2004). "Nanosecond pulsed electric fields perturb membrane phospholipids in T lymphoblasts." FEBS Lett. 572, 103-108.

[5] White, J. A., Blackmore, P. F., Schoenbach, K. H., and Beebe, S. J. (2004). "Stimulation of capacitative calcium entry in HL-60 cells by nanosecond pulsed electric fields." J. Biol. Chem 279, 22964-22972.

[6] Buescher, E. S., Smith, R. R., and Schoenbach, K. H. (2004). "Submicrosecond intense pulsed electric field effects on intracellular free calcium: Mechanisms and effects." IEEE Transactions on Plasma Science 32, 1563-1572.

[7] Beebe, S. J., Fox, P. M., Rec, L. J., Willis, E. L., and Schoenbach, K. H. (2003a). "Nanosecond, high-intensity pulsed electric fields induce apoptosis in human cells." FASEB J. 17, 1493-1495.

[8] Beebe, S. J., Blackmore, P. F., White, J., Joshi, R. P., and Schoenbach, K. H. (2004b). "Nanosecond pulsed electric fields modulate cell function through intracellular signal transduction mechanisms." Physiol Meas. 25, 1077-1093.

[9] Beebe, S. J., White, J., Blackmore, P. F., Deng, Y., Somers, K., and Schoenbach, K. H. (2003b). "Diverse effects of nanosecond pulsed electric fields on cells and tissues." DNA Cell Biol. 22, 785-796.

[10] Nuccitelli, R., Pliquett, U., Chen, X., Ford, W., Swanson, J., Beebe, S. J., Kolb, J. F., and Schoenbach, K. H. "Nanosecond pulsed electric fields cause melanomas to self-destruct." BBRC 343, 351 (2006).

[11] Feldman, Yu., Ermolina, I., and Hayashi, Y., (2003) "Time domain dielectric spectroscopy study of biological systems." IEEE Trans. Dielectrics and Electrical Insulation 10, pp. 728-753.

[12] Hu, Q., Joshi, R. P., and Schoenbach, K. H. (2005) "Simulations of nanopore formation and phosphatidylserine externalization in lipid membranes subjected to a high-intensity, ultrashort electric pulse." Phys. Rev. E. 72, 031902-1.

[13] Carey, W. J., and Mayes, J. R. (2003). "Marx Generator Design and Performance." Proc. Modulator Conf 2003, p. 625.

[14] Shu Xiao, Juergen Kolb, Muhammad A. Malik, Xinpei Lu, Mounir Laroussi, Ravindra P. Joshi, Edl Schamiloglu, Karl H. Schoenbach, "Electrical Breakdown and Dielectric Recovery of Polar Liquids", to appear in Trans. Plasma Science.

[15] S. Katsuki, H. Akiyama, A. Abou-Ghazala, and K. H. Schoenbach, "Parallel Streamer Discharges Between Wire and Plane Electrodes in Water," IEEE Trans. Dielectrics and Electrical Insulation 9, 498-506 (2002).

[16] S. Afford, and S. Randhawa, "Apoptosis," Mol. Path. 53, 55 (2000)

[17] Mayes, J. R. and Carey, W. J., "The Generation of High Electric Field Strength RF Energy Using Marx Generators, Proc. Modulator Conference." 2003, p. 236.

[18] Baum, C. E., (2005) "Producing Large Transient Electromagnetic Fields in a Small Region: An Electromagnetic Implosion, Sensor and Simulation Notes." Note 501, August 2005.

[19] Foster, K. R., (2000) "Thermal and Nonthermal Mechanisms of Interaction of Radio-Frequency Energy with Biological Systems." IEEE Trans. Plasma Science 28, 15.

[20] Andrei G. Pakhomov, Amy Phinney, John Ashmore, Kerfoot Walker III, Juergen Kolb, Susumu Kono, Karl H. Schoenbach, and Michael R. Murphy, "Characterization of the Cytotoxic Effect of High-Intensity, 10-ns Duration Electrical Pulses," IEEE Trans. Plasma Science 32, 1579-1586 (2004).

What is claimed is:

1. An apparatus comprising:
an electric field pulse generator for generating a pre-defined sequence of ultrashort voltage pulses;
an electric pulse radiator for generating electromagnetic waves based on the ultrashort voltage pulses; and,
a focusing device comprising at least one of a focusing reflector and a focusing lens for directing at least a portion of the electromagnetic waves to at least one target in a cell or tissue.

2. The apparatus of claim 1, wherein the electric pulse radiator comprises one or more antenna.

3. The apparatus of claim 2, wherein the focusing reflector comprises an ellipsoidal reflector.

4. The apparatus of claim 2, wherein the focusing reflector comprises a parabolic reflector.

5. The apparatus of claim 1, wherein the electric pulse generator generates between about 0.1 picosecond voltage pulses up to 900 nanosecond (ns) voltage pulses.

6. The apparatus of claim 1, wherein the electric pulse generator generates voltage pulses up to 2 MV.

7. The apparatus of claim 1, wherein the electric pulse radiator with the focusing device generates electric fields of 10 kV/cm to 800 kV/cm at the target.

8. The apparatus of claim 1, wherein the electric pulse generator generates voltage pulses with a pulse duration of less than or equal to 1 nanosecond (ns) and a voltage of less than or equal to 1 MV.

9. The apparatus of claim 1, wherein the electric pulse generator generates monopolar, bipolar, and oscillatory high voltage pulses with voltages from about 10 kV to 1 MV and pulse durations (half periods) ranging from about 10 ps to 5 ns.

10. The apparatus of claim 1, wherein the focusing device is configured to focusing the energy of the electrical pulses into one of a well defined volume in cell cultures, tissues and organs or over a large distance.

11. The apparatus of claim 1, wherein the electrical energy is delivered through a cable having at least two coaxial conductors to the at least one target in the cells or the tissues.

12. The apparatus of claim 1, further comprising:
one or more receptacles comprising the cells to be exposed to the ultrashort pulses;
an insulator;
a coaxial cable;
an ultrawideband exposure cell;
a current probe;
a capacitive voltage divider;
a screen room comprising an oscilloscope and trigger;
a Marx-Bank with about 20 to 30 stages in a pressurized containment;
a pulse forming network; and,
a tail cut switch.

13. A method of inducing apoptosis in cells and tissues comprising:
generating electromagnetic waves based on a pre-defined sequence of ultrashort voltage pulses;
focusing the electromagnetic waves onto cells or tissues in need of treatment to induce apoptosis or other programmed cell death in the cells or the tissues.

14. The method of claim 13, wherein the step of focusing further comprises focusing the electromagnetic waves onto abnormal cells or tissues so as to not affect normal cells.

15. The method of claim 13, wherein the electromagnetic waves are generated using at least one antenna.

16. The method of claim 13, wherein the electromagnetic waves are focused with at least one of a reflector and a lens.

17. The method of claim 13, wherein the pre-defined sequence comprises at least one pulse, at least once per day.

18. A method of treating a patient with cancer comprising:
generating electromagnetic waves based on a pre-defined sequence of ultrashort voltage pulses;
focusing the electromagnetic waves onto cells or tissues in the patient comprising cancer cells.

19. The method of claim 18, wherein the electromagnetic waves is focused onto abnormal cells or tissues comprising abnormal cells so as to not affect normal cells.

20. The method of claim 18, wherein the electromagnetic waves are generated using at least one antenna.

21. The method of claim 18, wherein the electromagnetic waves are focused with at least one of a reflector and a lens.

22. The method of claim 18, wherein the pre-defined sequence comprises at least one pulse, at least once per day.

23. A method of treating cells and tissues infected with an infectious disease organism comprising:
generating electromagnetic waves based on a pre-defined sequence of ultrashort voltage pulses;
focusing the electric field onto cells or tissues infected with an infectious disease organism.

24. The method of claim 23, wherein the electromagnetic waves are focused onto abnormal cells or tissues so as to not affect normal cells.

25. The method of claim 23, wherein the electromagnetic waves are generated using at least one antenna.

26. The method of claim 23, wherein the electromagnetic waves are focused with at least one of a reflector and a lens.

27. The method of claim 23, wherein the pre-defined sequence comprises at least one pulse, at least once per day.

28. A method of inducing calcium release in cells comprising:
generating electromagnetic waves based a pre-defined sequence of ultrashort voltage pulses; and
focusing the electromagnetic waves onto cells or tissues in need of treatment; and,
wherein the pre-defined sequence is selected to cause the electromagnetic waves to induce calcium release in cells.

29. A method of modifying cell structures and functions comprising:
    generating electromagnetic waves based on a pre-defined sequence of ultrashort voltage pulses; and
    focusing the electromagnetic waves onto cells or tissues in need of treatment,
    wherein the pre-defined sequence is selected to cause the electromagnetic waves to modify cell structures and functions.

30. The method of claim 29, wherein the cell structures are intracellular and extracellular.

31. The method of claim 29, wherein the cell structures comprise: mitochondria, endoplasmic reticulum, nucleus, nucleolus, Golgi apparatus, DNA, RNA, messenger RNA, proteins, DNA-protein interactions, RNA-protein interactions, protein-protein interactions, amino acids, lipids, lipid rafts, membrane receptors, and ion channels.

32. The method of claim 29, wherein the cell functions comprise:
    metabolism, transcription, translation, gene expression, secretion, neurotransmitter release, ion channel gating, apoptosis or other programmed cell death, cell cycle regulation, second messenger generation, enzyme activities, reactive oxygen species generation, oxidation/reduction reactions.

33. An apparatus comprising:
    at least one electric field pulse generator for generating one or more ultrashort voltage pulses; and
    a plurality of electrically isolated coaxial conductors defining a plurality of coaxial waveguides for said voltage pulses, each of said plurality of coaxial waveguides comprising two of said plurality of coaxial conductors arranged to cause electromagnetic waves to be generated in response to said voltage pulses.

34. The apparatus of claim 33, wherein said electric pulse generator is configured for generating a plurality of different voltage pulses for said plurality of coaxial waveguides.

35. The apparatus of claim 34, wherein said electric pulse generator is further configured for generating at least a first and a second of said plurality of voltage pulses to be shifted in phase with respect to each other.

36. The apparatus of claim 33, wherein the electric pulse generator generates between about 1 picosecond pulses up to 100 nanosecond (ns) pulses.

37. The apparatus of claim 33, wherein the electric pulse generator generates at least one of monopolar pulses, bipolar pulses, and oscillatory pulses.

38. A method, comprising:
    placing cells or tissues within a near field of a first end of a set of coaxial waveguides defined by a plurality of electrically isolated coaxial conductors; and
    applying a predefined sequence of voltage pulses to each of said coaxial waveguides so as to generate electromagnetic waves propagating into the cells or the tissues.

39. The method of claim 38, wherein said applying further comprises generating a plurality of different voltage pulses for each of said coaxial waveguides.

40. The method of claim 39, wherein at least a first and a second of said plurality of different voltage pulses are shifted in phase with respect to each other.

41. The method of claim 40, further comprising:
    selecting the phase shift between the plurality of different voltage pulses to obtain a highest electric field at the cells or tissues based on a modeling of the electric field distribution in the cells or tissues.

42. The method of claim 38, wherein said applying further comprises generating between about 1 picosecond voltage pulses up to 100 nanosecond (ns) pulses for said coaxial waveguides.

43. The method of claim 38, wherein said applying further comprises generates at least one of monopolar pulses, bipolar pulses, and oscillatory pulses for said coaxial waveguides.

44. The method of claim 38, further comprising:
    selecting a thickness and a separation of the plurality of coaxial conductors and a dielectric material between the plurality of coaxial conductors to obtain a highest electric field at the cells or tissues for the voltage pulses being applied.

* * * * *